(12) United States Patent
Galbraith et al.

(10) Patent No.: US 10,172,892 B2
(45) Date of Patent: Jan. 8, 2019

(54) STRAINS AND METHODS FOR ENERGY PARTITIONING IN RUMINANTS

(71) Applicant: DUPONT NUTRITION BIOSCIENCES APS, Copenhagen (DK)

(72) Inventors: Elizabeth Galbraith, Wauwatosa, WI (US); Keith Mertz, Neosho, WI (US); Ajay Awati, Swindon (GB)

(73) Assignee: DUPONT NUTRITION BIOSCIENCES APS (DK)

( * ) Notice: Subject to any disclaimer, the term of this patent is extended or adjusted under 35 U.S.C. 154(b) by 38 days.

(21) Appl. No.: 14/554,726

(22) Filed: Nov. 26, 2014

(65) Prior Publication Data

US 2015/0216916 A1 Aug. 6, 2015

Related U.S. Application Data

(63) Continuation-in-part of application No. 12/629,497, filed on Dec. 2, 2009, now abandoned.

(60) Provisional application No. 61/119,256, filed on Dec. 2, 2008.

(51) Int. Cl.

| | |
|---|---|
| A61K 35/74 | (2015.01) |
| A61K 35/742 | (2015.01) |
| C12R 1/07 | (2006.01) |
| C12R 1/46 | (2006.01) |
| A61K 35/744 | (2015.01) |
| A23K 10/16 | (2016.01) |
| A23K 10/18 | (2016.01) |
| A23K 50/10 | (2016.01) |

(52) U.S. Cl.
CPC ............ *A61K 35/742* (2013.01); *A23K 10/16* (2016.05); *A23K 10/18* (2016.05); *A23K 50/10* (2016.05); *A61K 35/744* (2013.01); *C12R 1/07* (2013.01); *C12R 1/46* (2013.01)

(58) Field of Classification Search
None
See application file for complete search history.

(56) References Cited

U.S. PATENT DOCUMENTS

| | | | |
|---|---|---|---|
| 5,529,793 | A | 6/1996 | Garner et al. |
| 5,534,271 | A | 7/1996 | Ware et al. |
| 2007/0071738 | A1 | 3/2007 | Rehberger et al. |
| 2008/0118472 | A1 | 5/2008 | Rode et al. |
| 2008/0233104 | A1 | 9/2008 | Farmer |
| 2010/0172873 | A1* | 7/2010 | Mertz .................. A61K 35/742 424/93.3 |

FOREIGN PATENT DOCUMENTS

| | | | |
|---|---|---|---|
| EP | 287699 | * | 7/1993 |
| EP | 0287699 | | 7/1993 |

OTHER PUBLICATIONS

Kung, http://dairy.ifas.ufl.edu/rns/2001/Kung.pdf, accessed Aug. 2, 2017.*
Al-Qumber et al., Journal of Applied Microbiology 101 (2006) 1152-1160.*
EP Search Report for Application No. 09531041.0 dated Jul. 4, 2013, 7 pages.
Beauchemin et al., Effects of bacterial direct-fed microbials and yeast on site and extent of digestions, blood chemistry, and subclinical ruminal acidosis in feedlot cattle; Journal of Animal Science 2003, 18: 1626-1640, 15 pages.
Proceedings of the 2009 Conference on Gastrointestinal Function, Chicago, USA, Apr. 20-22, Microb Ecol (2009), 57:562-588, 27 pages.
Nocek et al., Direct-Fed Microbial Supplementation on Ruminal Digestion, Health, and Performances of Pre- and Postpartum Dairy Cattle, American Dairy Science Association, J. Dairy Sci. 89:260-266, 7 pages.
Oetzel et al., Direct-Fed Microbial Supplementation and Health and Performances of Pre- and Postpartum Dairy Cattle: A Field Trial, American Dairy Science Association 2007, J. Dairy Sci. 90:2056-2068, 11 pages.
Osborne et al., Effects of Monensin on Ruminal Forage Degradability and Total Tract Diet Digestibility in Lactating Dairy Cows During Grain-Induced Subacute Ruminal Acidosis, American Dairy Science Association 2004, J. Dairy Sci.
ARS Culture Collection (NRLL) Database Server search results, Prokaryote, Bacillus, retrieved from internet url: http://nml.ncaur.usda.gov/ogi-bin/usda/process.html on Jan. 17, 2010, 2 pages.
ARS Culture Collection (NRLL) Database Server search results, Prokaryote, Enterococcus, retrieved from internet url: http://nml.nccaur.usda.gov/ogi-bin/usda/process.html on Jan. 17, 2010, 2 pages.
Allison, M.J., et al., 1975. Grain overload in cattle and sheep: Changes in microbial populations in the cecum and rumen. Amer. J. Vet Res. 36:181.
Dunlop, R.H., 1972. Pathogenesis of ruminant lactic acidosis. Adv. Vet Sci. Comp Med. 16:259.
Elam, C.J. 1976. Acidosis in feedlot cattle: Practical observations. J. Anim. Sci. 43:898.
Hungate, R.E., et al, 1952, Microbiological and physiological changes associated with acute indigestion in sheep. Cornell Vet. 42:423.
Muir, L.A., et al. 1981. Prevention of induced lactic acidosis in cattle by thiopeptin. J. Anim. Sci. 52:635.
Owens, F.N., et al. 1998. Acidosis in cattle: a review. J. Amin. Sci. 76:275-286.
Slyter, L.L. 1976. Influence of acidosis on rumen function. J. Anim. Sci. 43:910.

(Continued)

*Primary Examiner* — Irene Marx

(57) ABSTRACT

Described are strains including *Enterococcus faecium* strain 8G-1 (NRRL B-50173), *Enterococcus faecium* strain 8G-73 (NRRL B-50172), *Bacillus pumilus* strain 8G-134 (NRRL B-50174) and strains having all of the identifying characteristics of each of these strains. One or more of the strains can be used to reduce negative energy balance in a ruminant. They can also be used to improve other measures of ruminant health and/or performance. Methods of using the strains, alone and in combination, are described. Methods of making the strains are also provided.

5 Claims, 10 Drawing Sheets

(56) References Cited

OTHER PUBLICATIONS

Yang, W., 2004. Effects of direct-fed microbial supplementation on ruminal acidosis, digestibility, and bacterial protein synthesis in continuous culture. Animal Feed Science Technology, 114(4): 179-193.
Rolfe, K., et al. "Impact of a New Direct-Fed Microbial on Intake and Ruminal pH." Nebraska Beef Cattle Reports, Animal Science Department, University of Nebraska—Lincoln, 2009.
Galbraith, E.A., et al. "T382 Effect of direct-fed microbial (DFM) products on rumen bacterial communities in Holstein cows at 2 and 6 weeks postcalving." J. Anim. Sci. vol. 88, E-Suppl. 2 / J. Dairy Sci. vol. 93, E-Suppl. 1 / Poult. Sci. vol. 89, E-Suppl. 1 (2010) pp. 431.
Ferguson, J.D., et al, "1134 The influence of Bacillus pumitus 8G-134 on milk production of dairy cows in early lactation." J. Amin. Sci. vol. 88, E-Suppl. 2 / J. Dairy Sci. vol. 93, E-Suppl. 1 / Poult Sci. vol. 89, E-Suppl. 1 (2010) pp. 871.
Smith, X., et al. "Selection of rumen bacteria to modulate rumen function in cattle fed readily-fermentable carbohydrates," Rowett-INRA 2010: Gut Microbiology, in Aberdeen, Scotland, Jun. 23-25, 2010.
Dong, S.H., et al. "T344 The survival of Bacillus subtilis natto in rumen and douodenum of Holstein dairy cows" J. Anim. Sci. vol. 89, E-Suppl. 1 / J. Dairy Sci. vol. 94, E-Suppl. 1 pp. 382-383.
Kang, H,Y., et al. "T348 Effect of feeding Bacillus subtilis natto fermentation production on hindgut fermentation and microbiota of Holstein dairy cows," J. Anim. Sci. vol. 89, E-Suppl. 1 / J. Dairy Sci. vol. 94, E-Suppl. 1 pp. 384.
Peng, H., et al. "T350 Effect of feeding Bacillus subtilis natto fermentation production on milk production and composition, blood metabolites and rumen fermentation in early lactation dairy cows." J. Anim. Sci. vol. 89, E-Suppl. 1 / J. Dairy Sci. vol. 94, E-Suppl. 1 pp. 384-385.
Henning, P. H., et al. "Effect of ruminal administration of the lactate-utilizing strain Megasphaera elsdenii (Me) NCIMB 41125 on abrupt or gradual transition from forage to concentrate diets." Animal Feed Science and Technology 157 (2010) 20-29.
Henning, P.H., et al. "The potential of Megasphaera elsdenii isolates to control ruminal acidosis." Anirraal Feed Science and Technology 157 (2010) 13-19.
AU office action dated Jul. 19, 2011 for Pat. App. No. 2009322439.
International Search Report and written Opinion dated Mar. 4, 2010 for PCT App. No. PCT/US09/66392.
ATCC Advanced Ctalog Search on Jun. 18, 2012.
International Preliminary Report on Patentability dated Jun. 7, 2011 for PCT App. No. PCT/US2009/066392.

* cited by examiner

STRAINS AND METHODS FOR ENERGY PARTITIONING IN RUMINANTS

CROSS-REFERENCE TO RELATED APPLICATIONS

This application is a continuation-in-part application of U.S. patent application Ser. No. 12/629,497 filed Dec. 2, 2009, which claims priority under 35 U.S.C. § 119(e) to U.S. Provisional Patent Application No. 61/119,256, filed Dec. 2, 2008; each of which is hereby incorporated by reference in their entirety.

BIBLIOGRAPHY

Complete bibliographic citations of the references referred to herein by the first author's last name and year of publication can be found in the Bibliography section, immediately preceding the claims.

FIELD

The invention relates to strains and methods for controlling acidosis. More particularly, the invention relates to bacterial strains useful for improving ruminant health and/or performance and methods of making and using the strains.

BACKGROUND

The feeding of high concentrations of fermentable carbohydrate to ruminants has become a common practice in the beef and dairy cattle industry over the last 50 years. The need for improving the production efficiency and quality of meat has led to this trend. Improvements in production have not occurred without certain difficulties. Increasing the ruminant consumption of fermentable carbohydrate by feeding higher levels of cereal grains has resulted in increased incidence of metabolic disorders such as acidosis. The relationship between high concentrate consumption and ruminal acidosis has been well documented in reviews (Dunlop, 1972; Slyter, 1976). Many researchers have shown a decline in ruminal pH following the feeding of high levels of readily fermentable carbohydrate (RFC) to cattle and the subsequent disruption of ruminal microbiota and physiological changes occurring in the animal (Allison, et. al., 1975, Hungate et. al., 1952; Elam, 1976). Most have attributed this decline to an over production of organic acids by ruminal bacteria such as *Streptococcus bovis*. However, the effect of excessive carbohydrate on the ruminal microbiota that initiates this response has not been well documented.

In the past, intensive management of feeding has been the only method to combat acidosis. More specifically, grains are diluted with roughage and the increase in dietary concentrate percentage is carefully controlled in a step-wise method to ensure smooth transition to high levels of concentrate over a 14-21 day period. Most commercial feedlots formulate and deliver several "adaptation" diets that contain different ratios of grain to forage.

Although intensive feeding management is usually quite effective in controlling acidosis, it is very costly to the producer due to the high cost of producing, transporting, chopping forage, disposing of increased animal waste, and lower production efficiencies. Producers and feedlot managers need to implement strategies that will allow for efficient production of livestock fed high concentrate rations.

Other strategies have been to combine the use of adaptation diets with feeding antimicrobial components such as ionophores. Ionophores inhibit intake and reduce the production of lactic acid in the rumen by reducing the ruminal populations of gram-positive, lactic acid-producing organisms such as *Streptococcus bovis* and *Lactobacillus* spp. (Muir et al. 1981).

Although the usage of ionophores have reduced the incidence of acute acidosis in feedlots, consumer concern about the use of antibiotics in meat production and the need for feedlot managers to continually find ways to reduce costs while improving animal performance and carcass composition has led to the examination of alternative methods to reduce acidosis and improve feedlot cattle performance.

The use of direct-fed microbials as a method to modulate ruminal function and improve cattle performance has been gaining increased acceptance over the past 10 years. There are two basic direct-fed microbial technologies that are currently available to the beef industry for the control of ruminal acidosis: (1) using lactic acid producing DFM technology and (2) adding specific bacterial species capable of utilizing ruminal lactic acid. While the reported mode of action of each of these technologies is different, they both attempt to address the accumulation of ruminal lactic acid.

The first approach, i.e., using lactic acid producing DFM technology, attempts to increase the rate of ruminal lactic acid utilization by stimulating the native ruminal microbiota. As reported, the addition of relatively slow growing lactic acid producing bacteria, such as species of *Enterococcus*, produces a slightly elevated concentration of ruminal lactic acid. The gradual increase forces the adaptation of the ruminal microflora to a higher portion of acid tolerant lactic acid utilizers. However, these *Enterococcus* strains failed to adequately control and prevent acidosis.

The second approach, i.e., adding specific bacterial species capable of utilizing ruminal lactic acid, is based on the finding that species of *Propionibacterium* significantly minimize the accumulation of ruminal lactic acid during an acidosis challenge with a large amount of Readily Fermentable Carbohydrate (RFC). *Propionibacterium* are natural inhabitants of the rumen in both dairy and beef cattle and function in the rumen by using lactic acid to produce important volatile fatty acids like acetate and propionate.

Current DFM technologies developed to date have been developed based upon an antiquated microbiological understanding of the incidence of acidosis in the rumen. Until recently, methods of studying the microbial ecology of the rumen have relied on cultivation techniques. These techniques have been limited due to unknown growth requirements and unsuitable anaerobic conditions for many of the rumen microorganisms. Thus, ecological studies relying on these cultivation techniques have been based on a limited understanding of the rumen microbiota.

Current DFMs when used alone or with yeast to minimize the risk of ruminal acidosis and to improve utilization of a feedlot cattle diet containing high concentrate provide mixed results. However, a study of DFM strains *Propionibacterium* P15, and *Enterococcus faecium* EF212, and *E. faecium* EF212, fed alone or fed combined with a yeast, *Saccharomyces cerevisiae*, indicated that addition of DFM combined with or without yeast had no effect on preventing ruminal acidosis (Yang, W., 2004).

In view of the foregoing, it would be desirable to provide one or more strains to prevent and/or treat acidosis. It would be advantageous if the one or more strains also improved other measures of ruminant health and/or performance. It would also be desirable to provide methods of making and using the strains.

SUMMARY

The invention, which is defined by the claims set out at the end of this disclosure, is intended to solve at least some of the problems noted above. Isolated strains are provided, including *Enterococcus faecium* strain 8G-1 (NRRL B-50173), a strain having all of the identifying characteristics of *Enterococcus faecium* strain 8G-1 (NRRL B-50173), *Enterococcus faecium* strain 8G-73 (NRRL B-50172), a strain having all of the identifying characteristics of *Enterococcus faecium* strain 8G-73 (NRRL B-50172), *Bacillus pumilus* strain 8G-134 (NRRL B-50174), a strain having all of the identifying characteristics of *Bacillus pumilus* strain 8G-134 (NRRL B-50174), and combinations thereof.

Additionally provided is a combination including one or more of the strains listed above and monensin.

Also provided is a method of administering an effective amount of one or more of the strains listed above to an animal and a method of administering a combination including an effective amount of one or more of the strains listed above and monensin to an animal.

In at least some embodiments, the administration of the one or more strain to the animal provides at least one of the following benefits in or to the animal when compared to an animal not administered the strain: (a) reduces acidosis, (b) stabilizes ruminal metabolism as indicated by delayed lactic acid accumulation and prolonged production of volatile fatty acids, (c) recovers more quickly from acidosis challenge as measured by pH recovery and lactic acid decline, (d) reduces exhibition of clinical signs associated with acidosis (e) increased milk production in lactating dairy cows, (f) increased milk fat content in lactating dairy cows, (g) decreased somatic cell count (SCC) in lactating dairy cows, (h) improved immunological response and health as evidenced by decreased SCC and (i) increased efficiency of milk production in lactating dairy cows.

In one embodiment, the strains, compositions, and methods can be used with any animal including but not limited to a postpartum animal, a peripartum animal, bovine, cattle, bull, steer, heifer, calf, cow, dairy cow, postpartum dairy cow, peripartum dairy cow, ovine, sheep, llama, alpaca, caprine, goat, ruminants, porcine, pig, swine, hog, avian species, turkey, fowl, chicken, and hen.

Also provided is a method of making a direct-fed microbial. In the method, a strain selected from the group consisting of *Enterococcus faecium* strain 8G-1 (NRRL B-50173), *Enterococcus faecium* strain 8G-73 (NRRL B-50172), and *Bacillus pumilus* strain 8G-134 (NRRL B-50174) is grown in a liquid nutrient broth. The strain is separated from the liquid nutrient broth to make the direct-fed microbial. In at least some embodiments of the method, the strain is freeze dried.

Additionally provided is a method of making a direct-fed microbial. In the method, a strain selected from the group consisting of *Enterococcus faecium* strain 8G-1 (NRRL B-50173), *Enterococcus faecium* strain 8G-73 (NRRL B-50172), and *Bacillus pumilus* strain 8G-134 (NRRL B-50174) is grown in a liquid nutrient broth. The strain is separated from the liquid nutrient broth to make the direct-fed microbial. Monensin is added to the direct-fed microbial.

In one embodiment, the disclosure relates to a method for reducing negative energy balance in an animal comprising: (a) identifying an animal at risk for negative energy balance; and (b) administering to the animal identified in step (a) an effective amount of *Bacillus pumilus* strain 8G-134 (NRRL B-50174) or a strain having all of the identifying characteristics of *Bacillus pumilus* strain 8G-134 (NRRL B-50174) to reduce negative energy balance.

In yet another embodiment, the disclosure relates to a method for reducing incidence of disease in an animal comprising: (a) administering to the animal an effective amount of *Bacillus pumilus* strain 8G-134 (NRRL B-50174) or a strain having all of the identifying characteristics of *Bacillus pumilus* strain 8G-134 (NRRL B-50174) to reduce incidence of disease, wherein the disease is selected from the group consisting of ketosis, displaced abosmasums, retained placenta, mastitis, metritis, and pyometra.

In still yet another embodiment, the disclosure relates to a method for reducing inflammation in an animal comprising: (a) identifying an animal at risk for, or showing signs of, inflammation; and (b) administering to the animal identified in step (a) an effective amount of *Bacillus pumilus* strain 8G-134 (NRRL B-50174) or a strain having all of the identifying characteristics of *Bacillus pumilus* strain 8G-134 (NRRL B-50174) to reduce inflammation.

An advantage of the strains, compositions and methods disclosed herein is that administration of *B. pumilus* 8G-134 to animals improves energy balance.

An advantage of the strains, compositions and methods disclosed herein is that administration of *B. pumilus* 8G-134 to animals reduces negative energy balance.

An advantage of the strains, compositions and methods disclosed herein is that feeding *B. pumilus* 8G-134 reduces the levels of nonesterified fatty acids (NEFA) in animals while maintaining high milk production.

An advantage of the strains, compositions and methods disclosed herein is that feeding *B. pumilus* 8G-134 promotes changes in immune cell populations of an animal.

An advantage of the strains, compositions and methods disclosed herein is that feeding *B. pumilus* 8G-134 improves the immune response of an animal.

An advantage of the strains, compositions and methods disclosed herein is that feeding *B. pumilus* 8G-134 influences the energy partitioned between milk and body tissue promoting an appropriately balanced body condition, which may promote health and fertility in subsequent lactations.

BRIEF DESCRIPTION OF THE DRAWINGS

Preferred exemplary embodiments described herein are illustrated in the accompanying drawings, in which like reference numerals represent like parts throughout and in which:

FIG. 13A is a line graph depicting the association between dietary starch and *Bacillus pumilus* concentration on postpartum glucose levels; (13A) Glucose: $S^1$(P=0.56); $BP^2$(P=0.49); $S*BP^3$(P=0.66); $S*B*W^4$(P=0.97); SEM=2.37.

FIG. 13B is a line graph depicting the association between dietary starch and *Bacillus pumilus* concentration on postpartum NEFA levels; (13B) NEFA: $S^1$(P=0.29); $BP^2$(P=0.05); $S*BP^3$(P=0.33); $S*B*W^4$(P=0.33); SEM=68.8.

FIG. 13C is a line graph depicting the association between dietary starch and *Bacillus pumilus* concentration on postpartum BHBA levels; (13C) BHBA:$S^1$(P=0.92); $BP^2$(P=0.07); $S*BP^3$(P=0.41); $S*B*W^4$(P=0.50); SEM=2.57.

FIG. 13D is a line graph depicting the association between dietary starch and *Bacillus pumilus* concentration on postpartum haptoglobin levels; (13D) Haptoglobin: $S^1$(P=0.22); $BP^2$(P=0.66); $S*BP^3$(P=0.09); $S*B*W^4$(P=0.46). Interactions: [1]Starch; [2]*Bacillus pumilus*; [3]Starch and *Bacillus pumilus*; [4]Starch, *Bacillus pumilus* and week.

Figure 1:
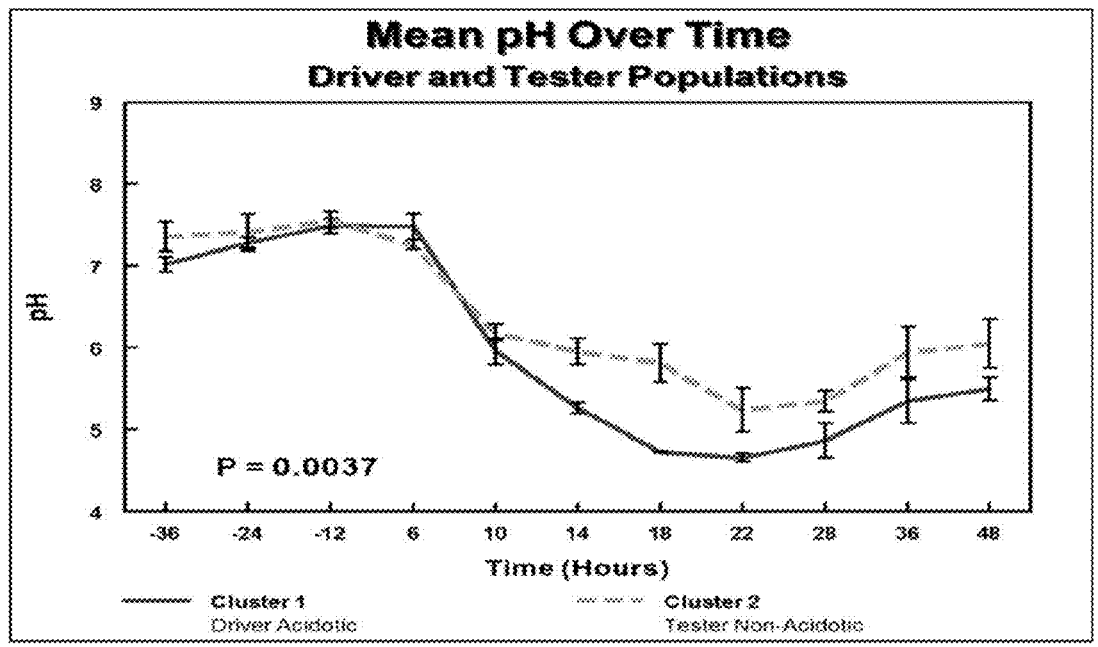
FIG. 1 is a graph showing pH differences between tester (non-acidotic; Cluster 2) and driver (acidotic; Cluster 1) populations.

Before explaining embodiments described herein in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure, which can be had by reference to the specification as a whole. Accordingly, the terms defined immediately below are more fully defined by reference to the specification as a whole.

It is noted that, as used in the specification and the appended claims, the singular forms "a," "an," and "the" include plural referents unless the context clearly dictates otherwise.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, "CD" (cluster differentiation) refers to molecules that are cell surface markers useful for the identification and characterization of leukocytes. The CD nomenclature was developed and is maintained through the HLDA (Human Leukocyte Differentiation Antigens) workshop.

By "administer," is meant the action of introducing at least one strain and/or supernatant from a culture of at least one strain described herein into the animal's gastrointestinal tract. More particularly, this administration is an administration by oral route. This administration can in particular be carried out by supplementing the feed intended for the animal with the at least one strain, the thus supplemented feed then being ingested by the animal. The administration can also be carried out using a stomach tube or any other way to make it possible to directly introduce the at least one strain into the animal's gastrointestinal tract.

As used herein, the term "effective amount" refers to the amount of the strain, strain combination or composition that will elicit the response including but not limited to biological or medical response of a tissue, system or animal that is being sought. In one embodiment, the term "effective amount" includes that amount of the strain, strain combination or composition that, when administered, is sufficient to prevent development of, or alleviate to some extent, one or more of the symptoms of the condition or disorder being treated. The effective amount may vary depending on the strain, strain combination or composition, the disorder or condition and its severity.

As used herein, the phrase "improving reproductive performance" refers to enhancing traits beneficial to reproduction and/or reducing traits, conditions, and/or diseases that impede reproduction. Improving reproductive performance includes but is not limited to reducing metritis, placental retention, mastitis, and postpartum diseases. Improving reproductive performance also includes reducing the reproductive cycle time.

As used herein, "negative energy balance" is a frequent condition occurring in dairy cows. It consists of an imbalance between diet energy supply and production requirement. Often during a state of negative energy balance, high milk production can come at the expense of body condition score, as fat and muscle are mobilized to support production. Loss of body condition is associated with altered blood metabolite and hormone profiles that may influence fertility.

As used herein, "performance" refers to the growth of an animal, such as a pig or poultry, measured by one or more of the following parameters: average daily gain (ADG), weight, scours, mortality, feed conversion, which includes both feed:gain and gain:feed, and feed intake. "An improvement in performance" or "improved performance" as used herein, refers to an improvement in at least one of the parameters listed under the performance definition.

As used herein, "prevent," "preventing," "prevention" and grammatical variations thereof refers to a method of partially or completely delaying or precluding the onset or recurrence of a disorder or condition and/or one or more of its attendant symptoms or barring an animal from acquiring or reacquiring a disorder or condition or reducing an animal's risk of acquiring or re-acquiring a disorder or condition or one or more of its attendant symptoms.

As used herein, the term "reducing" in relation to a particular trait, characteristic, feature, biological process, or phenomena refers to a decrease in the particular trait, characteristic, feature, biological process, or phenomena. The trait, characteristic, feature, biological process, or phenomena can be decreased by 5%, 10%, 15%, 20%, 25%, 30%, 35%, 40%, 45%, 50%, 55%, 60%, 65%, 70%, 75%, 80%, 85%, 90%, 95%, 100% or greater than 100%.

As used herein, "T cell population" includes regulatory T cells and effector T cells. T cell population includes both activated and un-activated T-cells. Cells within the T cell population may express a marker including but not limited to CD1, CD1a, CD1b, CD1c, CD1d, CD2, CD3, CD3d, CD3e, CD3g, CD4, CD5, CD6, CD7, CD8, CD8a, CD8b, CD9, CD11, CD11a, CD11b, CD11c, CD11d, CD13, CD16, CD17, CD18, CD20, CD21, CD23, CD25, CD26, CD27, CD28, CD29, CD30, CD31, CD32, CD32b, CD35, CD37, CD38, CD39, CD40L (also known as CD40 ligand), CD43, CD44, CD45, CD45R, CD45RA, CD45RB, CD45RC, CD45R0, CD45RHi, CD46, CD47, CD48, CD49a, CD49b, CD49c, CD49d, CD49e, CD49f, CD50, CD52, CD53, CD54, CD55, CD56, CD57, CD58, CD59, CD60a, CD62L, CD63, CD64, CD68, CD69, CD70, CD73, CD74, CD80, CD81, CD82, CD84, CD85A, CD85J, CD86, CD87, CD92, CD94, CD95, CD96, CD97, CD98, CD99, CD99R, CD100, CD101, CD102, CD103, CD107a, CD107b, CD108, CD109, CD119, CD120a, CD120b, CD121a, CD121b, CD122, CD124, CD126, CD127, CD129, CD130, CD132, CD134, CD137, CD146, Cd147, CD148, CD150, CD152, CD153, Cd154, CD156b, CD158a, CD158b1, CD158b2, CD158e, CD158f, CD158g, CD158h, CD158i, CD158j, CD158k, CD159a, CD159c, CD160, CD161, CD162, CD164, CD166, CD171, CD172g, CD178, CD181, CD182, CD183, CD184, CD185, CD186, CD191, CD192, CD193, CD194, CD195, CD196, CD197, CDw198, CDw199, CD200, CD205, CD210a, CDw210b, CD212, CD215, CD217, CD218a, CD218b, CD220, CD221, CD222, CD223, CD224, CD225, CD226, CD227, CD229, CD230, CD231, CD245, CD246, CD247, CD253, CD254, CD256, CD257, CD258, CD261, CD262, CD263, CD264, CD267, CD268, CD270, CD272, CD273, CD274, CD275, CD277, CD278, CD279, CD283, CD288, CD289, CD290, CD294, CD295, CD296, CD298, CD300a, CD300c, CD305, CD306, CD307c, Cd314, CD316, CD317, CD319, CD321, CD328, CD351, CD352, CD354, CD355, CD357, CD358, CD359, CD360, CD361, CD362, CD363 or an interleukin-2-receptor.

As used herein, "regulatory T cells" or "$T_{reg}$ cells" refer to T cells (T lymphocytes) that regulate the activity of other T cell(s) and/or other immune cells, usually by suppressing their activity. In one embodiment, the $T_{reg}$ cells are CD4$^+$, CD25$^+$, FoxP3$^+$ T-cells (but it will be appreciated by persons skilled in the art that $T_{reg}$ cells are not fully restricted to this phenotype).

As used herein, "effector T cells" or "$T_{eff}$ cells" refer to T cells (T lymphocytes) that carry out the function of an immune response, such as killing tumor cells and/or activating an anti-tumour immune-response that can result in clearance of the tumour cells from the body. In one embodiment, the $T_{eff}$ cells are CD3$^+$ with CD4$^+$ or CD8$^+$. $T_{eff}$ cells may secrete, contain or express effector markers such as IFN-gamma, granzyme B and ICOS (but it will be appreciated by persons skilled in the art that $T_{eff}$ cells are not fully restricted to these phenotypes)

As used herein, the terms "treat," "treating," "treatment" and grammatical variations thereof includes partially or completely delaying, alleviating, mitigating or reducing the intensity of one or more attendant symptoms of a disorder or condition and/or alleviating, mitigating or impeding one or more causes of a disorder or condition. Treatments according to the disclosure may be applied preventively, prophylactically, palliatively or remedially.

Provided herein are strains. Methods of making and using the strains are also provided.

In at least some embodiments, a direct-fed microbial (DFM) made with one or more of the strains provided herein allows beef and dairy producers to continue managing feeding regimens to optimize growth and performance without sacrificing health due to digestive upset associated with ruminal acidosis. At least some embodiments of the DFMs were selected on the basis of managing ruminal lactate concentrations via lactate utilization or priming the rumen to maintain lactate utilizing microflora. At least some embodiments of the DFMs were developed to manage ruminal energy concentrations. Unlike the current DFMs marketed to cattle producers to alleviate acidosis, at least some of the embodiments of the invention were not developed to manage a problem after it occurs, but rather to alleviate the problem before it happens.

Strains:

The strains provided herein include *Enterococcus faecium* strain 8G-1, *Enterococcus faecium* strain 8G-73, and *Bacillus pumilus* strain 8G-134, which are also referred to herein as 8G-1, 8G-73, and 8G-134, respectively.

Strains *Enterococcus faecium* strain 8G-1, *Enterococcus faecium* strain 8G-73, and *Bacillus pumilus* strain 8G-134 were deposited on Aug. 29, 2008 at the Agricultural Research Service Culture Collection (NRRL), 1815 North University Street, Peoria, Ill., 61604 and given accession numbers B-50173, B-50172, and B-50174, respectively. The deposits were made under the provisions of the Budapest Treaty on the International Recognition of the Deposit of Microorganisms for the Purposes of Patent Procedure. One or more strain provided herein can be used as a direct-fed microbial (DFM).

For purposes of this disclosure, a "biologically pure strain" means a strain containing no other bacterial strains in quantities sufficient to interfere with replication of the strain or to be detectable by normal bacteriological techniques. "Isolated" when used in connection with the organisms and cultures described herein includes not only a biologically pure strain, but also any culture of organisms which is grown or maintained other than as it is found in nature. In some embodiments, the strains are mutants, variants, or derivatives of strains 8G-1, 8G-73, or 8G-134 that also provide benefits comparable to that provided by 8G-1, 8G-73, and 8G-134. In some embodiments, the strains are strains having all of the identifying characteristics of strains 8G-1, 8G-73, or 8G-134. Further, each individual strain (8G-1, 8G-73, or 8G-134) or any combination of these strains can also provide one or more of the benefits described herein. It will also be clear that addition of other microbial strains, carriers, additives, enzymes, yeast, or the like will also provide control of acidosis and will not constitute a substantially different DFM.

Bacillus strains have many qualities that make them useful as DFMs. For example, several Bacillus species also have GRAS status, i.e., they are generally recognized as safe by the US Food and Drug Administration and are also approved for use in animal feed by the Association of American Feed Control Officials (AAFCO). The Bacillus strains described herein are aerobic and facultative sporeformers and thus, are stable. Bacillus species are the only sporeformers that are considered GRAS. A Bacillus strain found to prevent or treat acidosis is Bacillus pumilus strain 8G-134.

Enterococcus strains also have many qualities that make them useful as DFMs. Enterococcus strains are known to inhabit the gastrointestinal tract of monogastrics and ruminants and would be suited to survive in this environment. Enterococcus have been shown to be facultatively anaerobic organisms, making them stable and active under both aerobic and anoxic conditions. Enterococcus faecium strain 8G-1 and Enterococcus faecium strain 8G-73 were identified by the inventors as being useful for these purposes.

Agtech and Danisco USA Inc. of W227 N752 Westmound Dr. Waukesha, Wis. 53186, USA authorize DuPont Nutrition Biosciences ApS (formerly Danisco A/S) of Langebrogade 1, PO Box 17, DK-1001, Copenhagen K, Denmark to refer to these deposited biological materials in this patent application and have given unreserved and irrevocable consent to the deposited material being made available to the public.

Preparation of the Strains:

In at least one embodiment, each one of the strains described herein is cultured individually using conventional liquid or solid fermentation techniques. In at least one embodiment, the Bacillus strain and Enterococcus strains are grown in a liquid nutrient broth, in the case of the Bacillus, to a level at which the highest number of spores are formed. The Bacillus strain is produced by fermenting the bacterial strain, which can be started by scaling-up a seed culture. This involves repeatedly and aseptically transferring the culture to a larger and larger volume to serve as the inoculum for the fermentation, which can be carried out in large stainless steel fermentors in medium containing proteins, carbohydrates, and minerals necessary for optimal growth. Non-limiting exemplary media are MRS or TSB. However, other media can also be used. After the inoculum is added to the fermentation vessel, the temperature and agitation are controlled to allow maximum growth. In one embodiment, the strains are grown at 32° to 37° under agitation. Once the culture reaches a maximum population density, the culture is harvested by separating the cells from the fermentation medium. This is commonly done by centrifugation.

In one embodiment, to prepare the Bacillus strain, the Bacillus strain is fermented to a $5\times10^8$ CFU/ml to about $4\times10^9$ CFU/ml level. In at least one embodiment, a level of $2\times10^9$ CFU/ml is used. The bacteria are harvested by centrifugation, and the supernatant is removed. The pelleted bacteria can then be used to produce a DFM. In at least come embodiments, the pelleted bacteria are freeze-dried and then used to form a DFM. However, it is not necessary to freeze-dry the Bacillus before using them. The strains can also be used with or without preservatives, and in concentrated, unconcentrated, or diluted form.

The count of the culture can then be determined. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

Using the Strains:

In at least some embodiments, one or more strain is used to form a DFM. One or more carriers, including, but not limited to, sucrose, maltodextrin, limestone, and rice hulls, can be added to the strain.

To mix the strain(s) and carriers (where used), they can be added to a ribbon or paddle mixer and mixed preferably for about 15 minutes, although the timing can be increased or decreased. The components are blended such that a uniform mixture of the cultures and carriers result. The final product is preferably a dry, flowable powder, and may be formulated based upon the desired final DFM concentration in the end product.

In at least one embodiment of a method of making a DFM, a strain described herein is grown in a medium, such as a liquid nutrient broth. The strain is separated from the liquid nutrient broth to make the direct-fed microbial. The strain can be freeze dried after it is separated from the broth.

One or more of Enterococcus faecium strain 8G-1, Enterococcus faecium strain 8G-73, and Bacillus pumilus strain 8G-134 can be fed to animals to reduce or even eliminate the occurrence of acidosis. For this, an effective amount of one or more of these strains is administered to the animals. Upon administration to the animals, the strain(s) provides at least one of the following benefits in or to the animals: (a) reduces acidosis in the animals, (b) stabilizes ruminal metabolism as indicated by delayed lactic acid accumulation and prolonged production of volatile fatty acids, (c) recovers more quickly from acidosis challenge as measured by pH recovery and lactic acid decline, and (d) does not exhibit clinical signs associated with acidosis.

The animals can be cattle, including both beef cattle and dairy cattle, that is, one or more bull, steer, heifer, calf, or cow; goats; sheep; llamas; alpacas; other four-compartment stomached, and ruminant animals that may encounter ruminal imbalance when fed readily fermentable carbohydrate (RFC).

In at least one embodiment, when *Enterococcus faecium* strain 8G-1 or *Enterococcus faecium* strain 8G-73 is fed, the strain is administered to the animals at a level such that the animals are dosed daily with about $5 \times 10^8$ CFU/animal/day to about $5 \times 10^{10}$ CFU/animal/day. In at least one embodiment, when *Bacillus pumilus* strain 8G-134 is fed, the strain is administered to the animals at a level such that the animals are dosed daily with about $5 \times 10^8$ CFU/animal/day to about $5 \times 10^{10}$ CFU/animal/day. In at least one embodiment, two or more strains of *Enterococcus faecium* strain 8G-1, *Enterococcus faecium* strain 8G-73 and *Bacillus pumilus* strain 8G-134 are fed, and the strains are administered to the animals at a level such that the animals are dosed daily with about $5 \times 10^8$ CFU/animal/day to about $5 \times 10^{10}$ CFU/animal/day as the total dose of the combined strains. Other levels of one or more strains can be fed to the animals. The strain can be administered to the animals from about 30 days of age through the remainder of the adult ruminant productive life or for other time periods.

In at least one embodiment, the strain is fed as a direct-fed microbial (DFM), and the DFM is used as a top dressing on a daily ration. In addition, the strain can be fed in a total mixed ration, pelleted feedstuff, mixed in with liquid feed, mixed in a protein premix, delivered via a vitamin and mineral premix.

In at least one embodiment, the strain is fed as a DFM, and the DFM is fed in combination with Type A Medicated Article monensin (Rumensin®), with a daily dose about 50 mg to 660 mg per head. Monensin is fed to increase feed efficiency. Monensin, as an ionophore, creates permeability in bacterial cell membrane creating an ion imbalance between the intracellular and extracellular spaces. This response affects ruminal microbiota populations and influence feedstuff fermentation to improve livestock feed efficiency.

In at least one embodiment, the strain is fed as a DFM, and the DFM is fed in combination with Type A Medicated Article tylosin phosphate (Tylan®), with a daily dose of about 60 to 90 mg/head. Tylosin phosphate is fed to beef cattle to reduce liver abscesses caused by *Fusobacterium necrophorum* and *Actinomyces pyogenes*.

Methods for Reducing Incidence of Disease

In another embodiment, the strains, methods, and compositions disclosed herein can be used to reduce incidence of disease in an animal. In one embodiment, the strain is *Bacillus pumilus* 8G-134.

In one embodiment, the disclosure relates to a method for reducing incidence of disease in an animal comprising: administering to the animal an effective amount of a *Bacillus pumilus* 8G-134 (NRRL-B-50174) or a strain having all of the identifying characteristics of *Bacillus pumilus* 8G-134 (NRRL-B-50174) to reduce incidence of disease. In one embodiment, the animal is an animal selected from the group consisting of: a peripartum animal, a postpartum animal, or an animal in labor.

In one embodiment, the disclosure relates to a method for reducing incidence of disease in an animal comprising: administering to a peripartum animal an effective amount of a *Bacillus pumilus* 8G-134 (NRRL-B-50174) or a strain having all of the identifying characteristics of *Bacillus pumilus* 8G-134 (NRRL-B-50174) to reduce incidence of disease, wherein *Bacillus pumilus* 8G-134 (NRRL-B-50174) is administered for two weeks prior to labor and delivery. In another embodiment, *Bacillus pumilus* 8G-134 (NRRL-B-50174) is administered for four weeks prior to labor and delivery. In still another embodiment, *Bacillus pumilus* 8G-134 (NRRL-B-50174) is administered for six to eight weeks prior to labor and delivery. In still another embodiment, *Bacillus pumilus* 8G-134 (NRRL-B-50174) is administered for a time period including but not limited 1, 2, 3, 4, 5, 6, 7, 8, 9, 10, 11, 12, 13, 14, 15, and 16 weeks prior to labor and delivery.

In one embodiment, the disclosure relates to a method for reducing incidence of disease in an animal comprising: administering to a peripartum animal an effective amount of a *Bacillus pumilus* 8G-134 (NRRL-B-50174) or a strain having all of the identifying characteristics of *Bacillus pumilus* 8G-134 (NRRL-B-50174) to reduce incidence of disease, wherein *Bacillus pumilus* 8G-134 (NRRL-B-50174) is administered for a period of time prior to labor and delivery and for a period of time after labor and delivery. In one embodiment, the strain is administered for a time period including but not limited 1, 2, 3, 4, 5, 6, 7, 8, 9, 10, 11, 12, 13, 14, 15, and 16 weeks prior to labor and delivery. In another embodiment, the strain is administered for a time period including but not limited 1, 2, 3, 4, 5, 6, 7, 8, 9, 10, 11, 12, 13, 14, 15, and 16 weeks after labor and delivery.

In one embodiment, the disclosure relates to a method for reducing incidence of disease in an animal comprising: administering to a peripartum animal, a postpartum animal, or an animal in labor and delivery an effective amount of a *Bacillus pumilus* 8G-134 (NRRL-B-50174) or a strain having all of the identifying characteristics of *Bacillus pumilus* 8G-134 (NRRL-B-50174) to reduce incidence of disease, wherein *Bacillus pumilus* 8G-134 (NRRL-B-50174) is administered for two weeks postpartum. In another embodiment, *Bacillus pumilus* 8G-134 (NRRL-B-50174) is administered for four weeks postpartum. In still another embodiment, *Bacillus pumilus* 8G-134 (NRRL-B-50174) is administered for six to eight weeks postpartum. In still another embodiment, *Bacillus pumilus* 8G-134 (NRRL-B-50174) is administered for a time period including but not limited 1, 2, 3, 4, 5, 6, 7, 8, 9, 10, 11, 12, 13, 14, 15, and 16 weeks postpartum.

In one embodiment, the animal is a ruminant animal. In still another embodiment, the animal is a dairy cow. In yet another embodiment, the animal is a peripartum dairy cow, a dairy cow in the process of calving, or a postpartum dairy cow.

In one embodiment, the disease is selected from the group consisting of: ketosis (acetonaemia), displaced abomasums, retained placenta, metritis, an inflammatory disease, inflammation, and mastitis.

A. Ketosis

Ketosis is a metabolic state where most of the body's energy supply comes from ketone bodies in the blood, in contrast to a state of glycolysis where blood glucose provides most of the energy. It is almost always generalized, with hyperketonemia, that is, an elevated level of ketone bodies in the blood throughout the body. Ketone bodies are formed by ketogenesis when liver glycogen stores are depleted. The main ketone bodies used for energy are acetoacetate and β-hydroxybutyrate, and the levels of ketone bodies are regulated mainly by insulin and glucagon Most cells in the body can use both glucose and ketone bodies for fuel, and during ketosis free fatty acids and glucose synthesis (gluconeogenesis) fuel the remainder.

In glycolysis higher levels of insulin promote storage of body fat and block release of fat from adipose tissues, while in ketosis fat reserves are readily released and consumed. For this reason ketosis is sometimes referred to as the body's "fat burning" mode.

In dairy cattle, ketosis is a common ailment that usually occurs during the first weeks after giving birth to a calf. Ketosis is in these cases sometimes referred to as acetonemia. A study from 2011 revealed that whether ketosis is developed or not depends on the lipids a cow uses to create butterfat. Animals prone to ketosis mobilize fatty acids from adipose tissue, while robust animals create fatty acids from blood phosphatidylcholine (lecithin). Healthy animals can be recognized by high levels of milk glycerophosphocholine and low levels of milk phosphocholine.

B. Displaced Abomasum

The abomasum (or true stomach) normally lies on the floor of the abdomen, but can become filled with gas and rise to the top of the abdomen, when it is said to be "displaced." The abomasum is more likely to be displaced to the left (LDA) than the right (RDA). The majority of cases occur soon after calving. During pregnancy the uterus displaces the abomasum, so that after calving the abomasum has to move back to its normal position, increasing the risk of displacement.

Fifty to eighty percent of LDA are diagnosed within two weeks postpartum. Eighty to ninety percent of LDA are diagnosed within one month postpartum. Cows with LDA were at increased risk 50× for ketosis.

Displaced abomasum can also be caused by atony of the abomasum. If the abomasum stops contracting and turning over its contents, accumulation of gas will occur and the abomasum will tend to move up the abdomen. This tends to be a cause of inadequate nutrition.

Symptoms of displaced abomasum include but are not limited to loss of appetite; drop in milk yield; reduced rumination; and mild diarrhea.

C. Retained Placenta

Retained placenta (RP) is also known as retained fetal membrane or retained cleansing. RP occurs when the calf's side of the placenta (the fetal membranes) fails to separate from the mother's side. Separation of the membranes normally occurs after the calf is born (early separation is one cause of stillbirth). RP is usually defined as the failure to expel fetal membranes within 24 hr after parturition.

Retained placenta is most commonly associated with dystocia, milk fever (metabolic diseases) and twin births. The single sign associated with RP is degenerating, discolored, ultimately fetid membranes hanging from the vulva. Occasionally, the retained membranes may remain within the uterus and not be readily apparent, in which case their presence may be signaled by a foul-smelling discharge. Cows with retained fetal membranes are at increased risk of developing metritis, ketosis, mastitis, and even abortion in a subsequent pregnancy.

D. Mastitis

Mastitis occurs when white blood cells (leukocytes), are released into the mammary gland, usually in response to an invasion of bacteria of the teat canal. Milk-secreting tissue, and various ducts throughout the mammary gland can be damaged by toxins from bacteria. Mastitis can also occur as a result of chemical, mechanical, or thermal injury.

Mastitis in dairy cattle is the persistent, inflammatory reaction of the udder tissue. This potentially fatal mammary gland infection is the most common disease in dairy cattle in the United States. It is also the most costly to the dairy industry.

The inflammatory response results in an increase in the blood proteins and white blood cells in the mammary tissue, which can then pass into the milk product. This response aims to destroy the irritant, repair the damaged mammary tissue and return the udder to its normal function. However, as a result of such mastitis, a loss in milk output is often experience.

Methods for Reducing Negative Energy Balance of an Animal

Negative energy balance occurs for a variety of reasons including but not limited to a decrease in dry matter intake (DMI); an increase in energy demands due to milk production; and a lagging increase in DMI after parturition. Higher blood NEFA and beta-hydroxybutyrate (BHBA) are typical in the early postpartum period when cows are partitioning energy toward milk production, and are known to be negatively correlated with energy balance. Not to be bound by a particular theory, cows with greater NEFA are mobilizing more adipose tissue to support milk production and are losing more body condition (BC) relative to cows with lower NEFA levels. Adipose is mobilized as NEFA and transported to the liver to be oxidized or re-esterified into triglycerides. When re-esterification of triglycerides is increased, production of ketone bodies is increased. Ketone bodies include BHBA, acetoacetate, and acetone.

Lower levels of NEFA and/or BHBA likely indicate normal adjustment to the new energy demands, however, higher levels of NEFA and/or BHBA can be predictive of greater incidence of disease such as ketosis and displaced abomasums.

In one embodiment, the strains, methods, and compositions disclosed herein can be used to reduce negative energy balance of an animal. In one embodiment, the strain is *Bacillus pumilus* 8G-134.

In one embodiment, the disclosure relates to a method for reducing negative energy of an animal comprising: administering to the animal an effective amount of a *Bacillus pumilus* 8G-134 (NRRL-B-50174) or a strain having all of the identifying characteristics of *Bacillus pumilus* 8G-134 (NRRL-B-50174) to reduce negative energy balance of an animal.

In one embodiment, the animal is a ruminant animal. In yet another embodiment, the animal is a peripartum animal. In another embodiment, the animal is a postpartum animal. In still another embodiment, the animal is an animal in the process of labor and delivery. In still another embodiment, the animal is a dairy cow, a peripartum dairy cow, a postpartum dairy cow, or a dairy cow in the process of calving.

In one embodiment, the disclosure relates to a method for reducing negative energy of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) results in better milk production and body condition score as compared to animals not administered the strain.

In one embodiment, the disclosure relates to a method for reducing negative energy of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) results in lower levels of NEFA as compared to animals not administered the strain. In another embodiment, administration of *Bacillus pumilus* 8G-134 (NRRL-B-50174) results in lower levels of BHBA as compared to animals not administered the strain. In still another embodiment, administration of *Bacillus pumilus* 8G-134 (NRRL-B-50174) results in lower levels of NEFA and BHBA as compared to animals not administered the strain.

In one embodiment, the disclosure relates to a method for reducing negative energy of an animal comprising: obtaining a sample from an animal; determining the level of NEFA and/or BHBA in the sample; administering to an animal, with a level of NEFA and/or BHBA indicative of negative energy balance, an effective amount of *Bacillus pumilus* 8G-134 (NRRL-B-50174) or a strain having all of the identifying characteristics of *Bacillus pumilus* 8G-134 (NRRL-B-50174). In one embodiment, the sample is blood. In another embodiment, the sample is collected from a peri-parturient animal (from 14 days prepartum to 14 days postpartum). In one embodiment, samples are collected at time points to avoid diurnal and postprandial variations.

In one embodiment, the disclosure relates to a method for reducing negative energy of an animal comprising: obtaining a sample from numerous animals in a herd; determining the level of NEFA and/or BHBA in each sample obtained; administering an effective amount of *Bacillus pumilus* 8G-134 (NRRL-B-50174) or a strain having all of the identifying characteristics of *Bacillus pumilus* 8G-134 (NRRL-B-50174) to the herd when 10-25% of the sampled animals had NEFA and/or BHBA concentrations indicative of disease. In one embodiment, the strain is administered when 15% of the sampled animals had NEFA and/or BHBA concentrations indicative of disease.

In one embodiment, a level of NEFA in a prepartum animal greater than 0.27 mEq/l is indicative of negative energy balance.

In yet another embodiment, a level of NEFA in a postpartum animal greater than 0.70 mEq/l is indicative of negative energy balance.

In yet another embodiment, a level of BHBA in a postpartum animal greater than 12 mg/dL is indicative of negative energy balance.

In still another embodiment, the disclosure relates to a method for reducing negative energy of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) to the animal results in lower levels of NEFA and better milk production as compared to animals not administered the strain. In another embodiment, administration of *Bacillus pumilus* 8G-134 (NRRL-B-50174) results in lower levels of BHBA and better milk production as compared to animals not administered the strain. In still another embodiment, administration of *Bacillus pumilus* 8G-134 (NRRL-B-50174) results in lower levels of NEFA and BHBA and better milk production as compared to animals not administered the strain.

In one embodiment, administration of *Bacillus pumilus* 8G-134 (NRRL-B-50174) can increase milk production as compared to animals not administered the strain by a percentage selected from the group consisting of 0.1-0.5%, 0.5-1%, 1-3%, 3-5%, 5-7%, 7-9, 10%, 10-12%, 12-15%, 15-20%, 20-25%, 25-30%, 30-35%, and greater than 35%. In another embodiment, administration of *Bacillus pumilus* 8G-134 (NRRL-B-50174) can increase milk production as compared to animals not administered the strain by greater than 0.1%, greater than 0.3%, greater than 0.5%, greater than 1%, greater than 3%, greater than 5%, greater than 7%, or greater than 10%.

In one embodiment, administration of *Bacillus pumilus* 8G-134 (NRRL-B-50174) to an animal can decrease levels of NEFA in the animal as compared to an animal not administered the strain by a percentage selected from the group consisting of 0.1-1%, 1-5%, 5-10%, 10-15%, 15-20%, 20-25%, 25-30% 35-40%, 40-45%, 45-55%, 55-65%, 65-75%, 75-85%, 85-95%, and greater than 95%. In yet another embodiment, administration of *Bacillus pumilus* 8G-134 (NRRL-B-50174) to an animal can decrease levels of NEFA in the animal as compared to animals not administered the strain by a percentage selected from the group consisting of 1-10%, 10-20%, 20-40%, 40-60%, 60-80%, 80-100% and greater than 100%.

In one embodiment, administration of *Bacillus pumilus* 8G-134 (NRRL-B-50174) to an animal can decrease levels of BHBA in the animal as compared to an animal not administered the strain by a percentage selected from the group consisting of 0.1-1%, 1-5%, 5-10%, 10-15%, 15-20%, 20-25%, 25-30% 35-40%, 40-45%, 45-55%, 55-65%, 65-75%, 75-85%, 85-95%, and greater than 95%. In yet another embodiment, administration of *Bacillus pumilus* 8G-134 (NRRL-B-50174) to an animal can decrease levels of BHBA in the animal as compared to animals not administered the strain by a percentage selected from the group consisting of 1-10%, 10-20%, 20-40%, 40-60%, 60-80%, 80-100% and greater than 100%.

In still another embodiment, the disclosure relates to a method for reducing negative energy of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) to the animal reduces incidence of disease associated with negative energy balance. In another embodiment, administration of *Bacillus pumilus* 8G-134 (NRRL-B-50174) results in lower incidence of a disease including but not limited to subclinical ketosis, retained placenta, displaced abomasums, and mastitis.

Methods for Improving an Immune Response of an Animal

In one embodiment, the strains, methods, and compositions disclosed herein can be used to improve an immune response of an animal. In one embodiment, improving an immune response of an animal comprises changing the immune cell population of an animal. In one embodiment, improving an immune response of an animal comprises increasing expression of T-cell markers.

A. Methods for Changing an Immune Cell Population of an Animal

In one embodiment, the strains, methods, and compositions disclosed herein can be used for changing an immune cell population in an animal. In another embodiment, the strains, methods, and compositions disclosed herein can be used for inducing changes in the immune cell population of a ruminant animal. In one embodiment, the strain is *Bacillus pumilus* 8G-134.

In one embodiment, changing the immune cell population of an animal comprises altering the expression pattern of the immune cells without an increase in total immune cell population.

In one embodiment, the disclosure relates to a method for inducing a change in the in immune cell population of an animal comprising: (a) identifying an animal in need of a change in immune cell population; and (b) administering to the animal an effective amount of a *Bacillus pumilus* 8G-134 (NRRL-B-50174) or a strain having all of the identifying characteristics of *Bacillus pumilus* 8G-134 (NRRL-B-

50174) to induce a change in the immune cell population. In one embodiment, an animal in need of a change in immune cell population is an animal at risk for disease and/or infection or an animal showing signs of disease and/or infection.

In one embodiment, the immune cell population is leukocytes.

Leukocytes (white blood cells) are classified into two major lineages: the myeloid leukocytes and the lymphocytes. The white cells of the myeloid lineage include neutrophils, monocytes, eosinophils and basophils. The white cells of the lymphocytes include T cells, B cells and natural killer cells.

In one embodiment, the ruminant animal is a dairy cow. In yet another embodiment, the ruminant animal is a postpartum dairy cow.

In one embodiment, a ruminant animal in need of a change in leukocyte population is an animal with a disease or infection. The disease or infection can be acute or chronic. In one embodiment, the disease is selected from the group consisting of ketosis (acetonaemia), displaced abomasums, retained placenta, and mastitis.

1. Methods for Inducing Changes in T Cell Population

In one embodiment, strains, methods, and compositions are disclosed for changing T-cell population subsets. In another embodiment, strains, methods, and compositions are disclosed for inducing changes in T-cell population subsets. In one embodiment, a change in T-cell population is reflected by an increase in expression of T cell CD markers, including but not limited to CD4, CD8, CD25, CD45R, CD45R0, CD62L, and CD45RHi. In one embodiment, the strain is *Bacillus pumilus* 8G-134. In one embodiment, T cells are one of the cell populations playing major roles in the immune system as a biodefence system against various pathogens. Such T cells are roughly classified into CD4 positive helper T cells and CD8 positive cytotoxic T cells, where the former relates to the promotion of immune response and the latter relates to the exclusion of virus-infected cells and tumor cells. Helper T cells are further classified into Type I helper T cells for promoting cellular immunity and Type II helper T cells for promoting humoral immunity. These T cells with such diversified properties have a function of excluding pathogens and gaining infection resistance under a well-balanced immune response.

In one embodiment, the disclosure relates to a method for inducing a change in the T cell population of an animal comprising; (a) identifying an animal in need of a change in T cell population; and (b) administering to the animal an effective amount of a *Bacillus pumilus* 8G-134 (NRRL-B-50174) or a strain having all of the identifying characteristics of *Bacillus pumilus* 8G-134 (NRRL-B-50174) to induce a change in the T cell population. In one embodiment, a change in T cell population is evident by an increase in expression of T cell CD markers, including but not limited to CD4, CD8, CD25, CD45R, CD45R0, CD62L, and CD45RHi.

In one embodiment, the disclosure relates to a method for inducing a change in the T cell population of an animal comprising: (a) obtaining a sample from an animal; (b) determining an initial T cell population in the sample from the animal; and (c) administering to the animal an effective amount of a *Bacillus pumilus* 8G-134 (NRRL-B-50174) or a strain having all of the identifying characteristics of *Bacillus pumilus* 8G-134 (NRRL-B-50174) to induce a change in the T cell population. In yet another embodiment, the method further comprises (d) determining the T-cell population in a second sample from the animal after administration of *Bacillus pumilus* 8G-134 (NRRL-B-50174).

In one embodiment, a change in T-cell population is shown by a change in cell surface markers. In one embodiment, the cell surface marker is selected from the group consisting of CD4, CD8, CD45R, CD45R0, CD62L, and CD45RHi.

B. Methods for Improving Immune Response to Infection

The mucosal surfaces represent the largest area of exposure of the body to external pathogens. Immunoglobulin A (IgA), in its secretory form, is the main effector of the mucosal immune system and provides an important first line of defense against most pathogens that invade the body at a mucosal surface.

Secretory IgA (SIgA) represents the most abundant immunoglobulin of body secretions such as saliva, tears, colostrum and gastrointestinal secretions. The molecular stability and effector immune functions make SIgA particularly well suited to provide mucosal protection against pathogens.

IgA mediates a variety of protective functions. Luminal SIgA is believed to interfere with pathogen adherence to mucosal epithelial cells, a process called immune exclusion. In addition, IgA appears to have two other defense functions: intracellular neutralization, and virus excretion. IgA is also found as a monomer in the serum where it may function as a second line of defence by eliminating pathogens that have breached the mucosal surface. Serum IgA interacts with an Fc receptor called Fc$\alpha$R1 triggering antibody-dependent-cell-mediated cytotoxicity (ADCC).

In one embodiment, the strains, methods, and compositions disclosed herein can be used to improve immune response of an animal to an infection. In one embodiment, the strain is *Bacillus pumilus* 8G-134.

In one embodiment, the disclosure relates to a method for improving immune response of an animal to an infection comprising: administering to the animal an effective amount of a *Bacillus pumilus* 8G-134 (NRRL-B-50174) or a strain having all of the identifying characteristics of *Bacillus pumilus* 8G-134 (NRRL-B-50174) to improve the immune response of an animal to an infection.

In yet another embodiment, the strain is administered for a period of time prior to labor and delivery including but not limited to 1, 2, 3, 4, 5, 6, 7, 8, 9, 10, 11, 12, 13, 14, 15, and 16 weeks prior to labor and delivery.

In yet another embodiment, the strain is administered for a period of time post labor and delivery including but not limited to 1, 2, 3, 4, 5, 6, 7, 8, 9, 10, 11, 12, 13, 14, 15, and 16 weeks post labor and delivery.

In another embodiment, the strain is administered within the first two weeks post-calving. In yet another embodiment, the strain is administered within the first week post calving.

In another embodiment, the strain is administered two weeks prior to calving. In yet another embodiment, the strain is administered one week prior to calving.

In one embodiment, the disclosure relates to a method for improving immune response of an animal comprising: administering to the animal an effective amount of a *Bacillus pumilus* 8G-134 (NRRL-B-50174) or a strain having all of the identifying characteristics of *Bacillus pumilus* 8G-134 (NRRL-B-50174), wherein an increase in IgA as compared to animals not administered the strain is indicative of an improved immune response. An increase of IgA in the milk during the first week post-calving can provide improved immune defense in the mammary gland to prevent bacterial adhesion and invasion of mammary epithelial cells. It would also be expected to provide a benefit to the calf, boosting calf health through passive transfer of immunity.

In one embodiment, the disclosure relates to a method for improving immune response of an animal comprising: obtaining a sample from an animal; determining the level of IgA in the sample; administering to an animal, with a level of IgA indicative of a suppressed immune response, an effective amount of *Bacillus pumilus* 8G-134 (NRRL-B-50174) or a strain having all of the identifying characteristics of *Bacillus pumilus* 8G-134 (NRRL-B-50174). In one embodiment, the sample is blood. In another embodiment, the sample is collected from a peri-parturient animal (from 14 days prepartum to 14 days postpartum).

In one embodiment, administration of *Bacillus pumilus* 8G-134 (NRRL-B-50174) to an animal can increase levels of IgA in the animal as compared to an animal not administered the strain by a percentage selected from the group consisting of 1-5%, 5-10%, 10-15%, 15-20%, 20-25%, 25-30% 35-40%, 40-45%, 45-55%, 55-65%, 65-75%, 75-85%, 85-95%, and greater than 95%. In yet another embodiment, administration of *Bacillus pumilus* 8G-134 (NRRL-B-50174) to an animal can increase levels of IgA in the animal as compared to an animal not administered the strain by a percentage selected from the group consisting of 1-10%, 10-20%, 20-40%, 40-60%, 60-80%, 80-100% and greater than 100%. In one embodiment, the level of IgA in a treated animal as compared to an untreated animal is increased by 10-30%. In one embodiment, the level of IgA in a treated animal as compared to an untreated animal is increased by at least 15%.

Methods for Improving Reproductive Performance of an Animal

In one embodiment, the strains, methods, and compositions disclosed herein can be used to improve reproductive performance an animal. In one embodiment, the strain is *Bacillus pumilus* 8G-134.

In one embodiment, the disclosure relates to a method for improving reproductive performance of an animal comprising: administering to the animal an effective amount of a *Bacillus pumilus* 8G-134 (NRRL-B-50174) or a strain having all of the identifying characteristics of *Bacillus pumilus* 8G-134 (NRRL-B-50174) to improve reproductive performance of an animal.

In one embodiment, the animal is a ruminant animal. In still another embodiment, the animal is a dairy cow. In yet another embodiment, the animal is a postpartum dairy cow.

In one embodiment, the disclosure relates to a method for improving reproductive performance of an animal comprising: administering to a postpartum animal an effective amount of a *Bacillus pumilus* 8G-134 (NRRL-B-50174) or a strain having all of the identifying characteristics of *Bacillus pumilus* 8G-134 (NRRL-B-50174) to improve reproductive performance of an animal. In one embodiment, the postpartum animal had been diagnosed with a disease including but not limited to ketosis (acetonaemia), displaced abomasums, retained placenta, and mastitis.

In still another embodiment, *Bacillus pumilus* 8G-134 (NRRL-B-50174) is administered for a time period including but not limited 1, 2, 3, 4, 5, 6, 7, 8, 9, 10, 11, 12, 13, 14, 15, 16, 16-20, 20-24, 24-28, 28-32, 32-36, 36-40, 40-44, 44-48, 48-52, and greater than 52 weeks postpartum.

After calving, it typically takes about 60 to 90 days for a cow to resume cycles. This period is called postpartum anestrous. In first calf heifers, postpartum anestrous lasts longer than mature cows. It normally takes about 90 to 120 days for first calf heifers to resume cycles.

In one embodiment, the disclosure relates to a method for improving reproductive performance of an animal comprising: administering to a postpartum animal an effective amount of a *Bacillus pumilus* 8G-134 (NRRL-B-50174) or a strain having all of the identifying characteristics of *Bacillus pumilus* 8G-134 (NRRL-B-50174) to improve reproductive performance of an animal, wherein animals administered *Bacillus pumilus* 8G-134 (NRRL-B-50174) resume cycles sooner than animals not administered the strain. In one embodiment, animals administered the strain resume cycles 1-5, 5-10, 10-15, 15-20, 20-25, 25-30, 30-35, 35-40, 40-45, 45-50, 50-55, 55-60, 60-65, 65-70, 70-75, and 75-80 days sooner than animals not administered the strain.

In another embodiment, animals administered *Bacillus pumilus* 8G-134 (NRRL-B-50174) achieve a subsequent fertilization quicker than animals not administered the strain. In one embodiment, the animal administered the strain achieves a subsequent fertilization 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, and 85-90%, 90-95%, 95-100%, and greater than 100% sooner than animals not administered the strain.

In one embodiment, the disclosure relates to a method for improving reproductive performance of an animal comprising: administering to a postpartum animal an effective amount of a *Bacillus pumilus* 8G-134 (NRRL-B-50174) or a strain having all of the identifying characteristics of *Bacillus pumilus* 8G-134 (NRRL-B-50174), wherein animals administered *Bacillus pumilus* 8G-134 (NRRL-B-50174) have an increased number of conceptions as compared to animals not administered the strain. In one embodiment, animals administered *Bacillus pumilus* 8G-134 (NRRL-B-50174) have 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, 95-100%, and greater than 100% more conceptions than animals not administered the strain.

Methods for Reducing Inflammation

Acute-phase proteins are a class of proteins whose plasma concentrations increase (positive acute-phase proteins) or decrease (negative acute-phase proteins) in response to inflammation. This response is called the acute-phase reaction (also called acute-phase response). Two positive acute-phase proteins are haptoglobin and serum amyloid A. Haptoglobin is an inflammatory marker, and when an animal has an infection or inflammation that causes tissue damage, the animal's liver produces haptoglobin in abundance. High haptoglobin levels have been reported in the blood of animals with mastitis, metritis, pyometra, traumatic reticulitis, absomasal displacement, traumatic pericarditis, bacterial nephritis, and hepatic lipidosis.

In one embodiment, the strains, methods, and compositions disclosed herein can be used to reduce inflammation in an animal. In one embodiment, the strain is *Bacillus pumilus* 8G-134.

In one embodiment, the disclosure relates to a method for reducing inflammation of an animal comprising: administering to the animal an effective amount of a *Bacillus pumilus* 8G-134 (NRRL-B-50174) or a strain having all of the identifying characteristics of *Bacillus pumilus* 8G-134 (NRRL-B-50174) to reduce inflammation of an animal.

In one embodiment, the animal is a ruminant animal. In still another embodiment, the animal is a dairy cow. In yet another embodiment, the animal is a peripartum dairy cow, a dairy cow in the process of calving, or a postpartum dairy cow.

In one embodiment, the disclosure relates to a method for reducing inflammation of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) reduces inflammation as compared to animals not administered the strain.

In one embodiment, the disclosure relates to a method for reducing inflammation of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) increases levels of negative acute phase proteins as compared to animals not administered the strain.

In one embodiment, the disclosure relates to a method for reducing inflammation of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) reduces levels of positive acute phase proteins as compared to animals not administered the strain. In one embodiment, the positive acute phase proteins are haptoglobin and serum amyloid A.

In one embodiment, the disclosure relates to a method for reducing inflammation of an animal comprising: administering to an animal an effective amount of *Bacillus pumilus* 8G-134 (NRRL-B-50174) or a strain having all of the identifying characteristics of *Bacillus pumilus* 8G-134 (NRRL-B-50174), wherein administration of *Bacillus pumilus* 8G-134 (NRRL-B-50174) results in a decrease in haptoglobin and/or serum amyloid A levels as compared to animals not administered the strain.

In one embodiment, the disclosure relates to a method for reducing inflammation of an animal comprising: obtaining a sample from an animal; determining the level of one or more acute phase proteins in the sample; administering to an animal, with a level of one or more acute phase proteins indicative of inflammation, an effective amount of *Bacillus pumilus* 8G-134 (NRRL-B-50174) or a strain having all of the identifying characteristics of *Bacillus pumilus* 8G-134 (NRRL-B-50174). In one embodiment, the sample is blood. In another embodiment, the sample is collected from a peri-parturient animal (from 14 days prepartum to 14 days postpartum). In one embodiment, samples are collected at time points to avoid diurnal and postprandial variations.

In one embodiment, administration of *Bacillus pumilus* 8G-134 (NRRL-B-50174) to an animal can decrease levels of one or more acute phase proteins in the animal as compared to an animal not administered the strain by a percentage selected from the group consisting of 0.1-1%, 1-5%, 5-10%, 10-15%, 15-20%, 20-25%, 25-30% 35-40%, 40-45%, 45-55%, 55-65%, 65-75%, 75-85%, 85-95%, and greater than 95%. In yet another embodiment, administration of *Bacillus pumilus* 8G-134 (NRRL-B-50174) to an animal can decrease levels of one or more acute phase proteins in the animal as compared to animals not administered the strain by a percentage selected from the group consisting of 1-10%, 10-20%, 20-40%, 40-60%, 60-80%, 80-100% and greater than 100%.

In one embodiment, administration of *Bacillus pumilus* 8G-134 (NRRL-B-50174) to an animal can decrease levels of haptoglobin in the animal as compared to an animal not administered the strain by a percentage selected from the group consisting of 0.1-1%, 1-5%, 5-10%, 10-15%, 15-20%, 20-25%, 25-30% 35-40%, 40-45%, 45-55%, 55-65%, 65-75%, 75-85%, 85-95%, and greater than 95%. In yet another embodiment, administration of *Bacillus pumilus* 8G-134 (NRRL-B-50174) to an animal can decrease levels of haptoglobin in the animal as compared to animals not administered the strain by a percentage selected from the group consisting of 1-10%, 10-20%, 20-40%, 40-60%, 60-80%, 80-100% and greater than 100%.

In one embodiment, administration of *Bacillus pumilus* 8G-134 (NRRL-B-50174) to an animal can decrease levels of serum amyloid A in the animal as compared to an animal not administered the strain by a percentage selected from the group consisting of 0.1-1%, 1-5%, 5-10%, 10-15%, 15-20%, 20-25%, 25-30% 35-40%, 40-45%, 45-55%, 55-65%, 65-75%, 75-85%, 85-95%, and greater than 95%. In yet another embodiment, administration of *Bacillus pumilus* 8G-134 (NRRL-B-50174) to an animal can decrease levels of serum amyloid A in the animal as compared to animals not administered the strain by a percentage selected from the group consisting of 1-10%, 10-20%, 20-40%, 40-60%, 60-80%, 80-100% and greater than 100%.

EXAMPLES

The following Examples are provided for illustrative purposes only. The Examples are included herein solely to aid in a more complete understanding of the presently described invention. The Examples do not limit the scope described herein described or claimed herein in any fashion.

Example 1

Acidosis Model Experimental Design:

Ten crossbred steers were blocked by weight and assigned to two pens. The daily feed ration for all treatment groups prior to challenge consisted of 45% roughage and 55% concentrate on a dry matter basis. Cattle were fed 15 lbs/head/day of the ration once in the morning and had remaining feed pushed closer to the feeding stanchion late in the afternoon. Both pens were fasted for 24 hours before challenge with the concentrate diet treatments. Concentrate diet treatments consisted of highly fermentable carbohydrate sources of steam flaked corn on a 90% as fed basis. After fasting for 24 hours, the concentrate diet was fed ad libitum at 100 lbs/pen to all pens (0 h). Challenge diet consumption was visually monitored and additional feed added on an as needed basis.

Rumen fluid samples were obtained from individual animals via oral intubation using a collection tube attached to a vacuum flask. Different flasks and collection tubes were used for each pen to minimize cross contamination of microbiota between treatments. Ruminal fluid collected in the vacuum flasks was decanted into sterile 50 ml Falcon tubes labeled with sample time and animal identification number (ear tag number). Ruminal samples were collected from all pens at −36 h, −24 h, and −12 h. Time −36 h and −24 h samples represented the physiological baseline for each animal. Time −12 h samples represented rumen fluid in the fasted state for each animal. Time 0h was designated as the beginning of the feeding challenge. Ruminal samples were collected from all animals every 4 hours from +6 to +22 hours. All pens were sampled at +28, +36, and +48 hours. The pH from individual ruminal samples were analyzed immediately after acquisition. All samples were frozen and prepared for shipment to Agtech Products, Inc. (Waukesha, Wis.) for further analysis.

Volatile fatty acids and carbohydrate concentrations were measured in individual ruminal samples. Samples were prepared for HPLC analysis by aseptically removing duplicate 1.0 ml samples from the rumen fluid collected from each animal at each time period. Samples were placed in a 1.5 ml microcentrifuge tube and the debris was pelleted by centrifugation (10 minutes, at 12,500 rpm). The supernatant fluid (750 µl) was transferred to a clean tube and acidified with an equal volume of 5 mM $H_2SO_4$. The acidified fluid was thoroughly mixed and filtered through 0.2 µm filter directly into a 2 ml HPLC autosampler vial and capped. Samples were analyzed using a Waters 2690 HPLC system (Waters Inc., Milford, Mass.). The sample were injected into 5 mM $H_2SO_4$ mobile phase heated to 65° C. and separated using a BioRad HPX-87H Column (Bio-Rad Laboratories, Inc., Hercules, Calif.). The HPLC was standardized using a set of concentrations for each compound of interest. Compounds used as standards were include dextrose (glucose), lactate, methylglyoxal, butyrate, propionate, and acetate.

Figure 2:
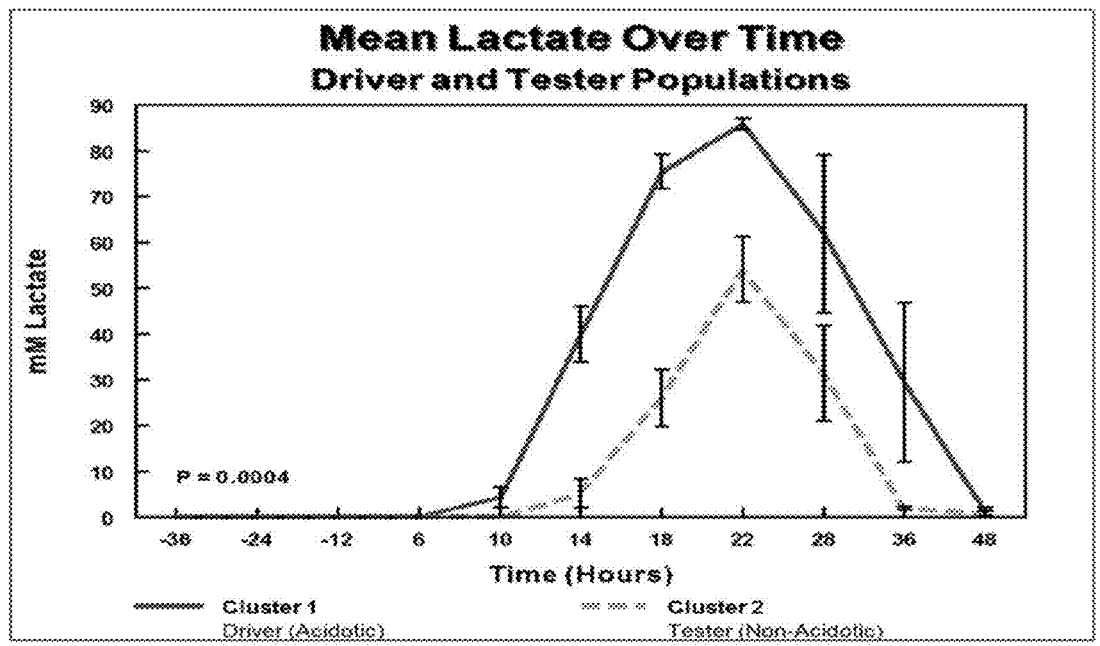
FIG. 2 is a graph showing lactic acid accumulation differences between tester (non-acidotic; Cluster 2) and driver (acidotic; Cluster 1) populations.

Discovery of Bacterial Genes in Non-Acidotic Cattle Ruminal Microflora: Suppressive Subtractive Hybridization:

The Genome Subtraction Kit (Clontech, Palo Alto, Calif.) was utilized to determine microbial population differences between two sets of pooled ruminal samples. Hierarchal clustering analysis was performed to determine similarities and differences between animals based on pH and lactic acid profiles over time. Cluster analysis positioned cattle 2069, 2071, 2078, 2113, and 2127 in Cluster 1 and cattle 2107, 2115, 2088, 2133, and 2124 in Cluster 2. Repeated measures analysis was performed to compare pH and lactic acid from Cluster 1 to Cluster 2. All variables were analyzed separately. Cluster 1 had a significantly higher mean lactic acid profile than Cluster 2 ($P=0.0004$) accompanied with lower mean pH ($P=0.0075$) throughout the course of the challenge diet period (FIGS. 1 and 2). The rumen fluid from individual animal was pooled within cluster for suppressive subtractive hybridization (SSH) procedures.

Suppressive subtraction hybridization (SSH) strategies were developed to compare pooled ruminal DNA samples from cattle in Cluster 1 to those in Cluster 2 at sample times +6 h, +10 h, +14 h, and +18 h. Suppressive subtraction hybridization was performed utilizing Cluster 2 as the tester (non-acidotic cattle) and Cluster 1 as the driver (acidotic cattle). The SSH was hypothesized to result in unique DNA fragments from organisms that resulted in lower levels of lactic acid and a higher pH (ruminal energy modulating organism). By performing subtractions using samples from time +10 h, the DNA fragments (genes) found, were from organisms that were able to modulate the utilization of excess energy in the ruminal environment in the form of RFC and alleviate potential effects of acidosis.

Cloning and Screening of Unique Tester Sequence Library:

Strain specific DNA sequences that are recovered after subtraction were cloned for further analysis. DNA sequences were inserted into the pCR2.1 vector (Invitrogen) and transformed into E. coli chemically competent TOP10 cells. The transformation mixture was plated onto 22×22 cm LB agar plates containing 50 µg/ml kanamycin and overlaid with 40 mg/ml X-gal in DMF. Plates were incubated at 37° C. for 24 h. Recombinant colonies (white colonies) were picked into sterile microtitre plates containing LB medium and kanamycin at 50 µg/ml. All wells containing recombinant PCR products were separated into 1 ml aliquots. One aliquot was purified using the Qiaquick PCR Purification Kit (Qiagen), with the second aliquot pelleted via centrifugation, resuspended in LB+Kan+10% glycerol and stored at −80° C.

Southern Hybridization:

Slot-blot hybridizations were conducted using standard protocols. To confirm the specificity of the cloned DNA inserts, positively charged Zeta-Probe® Blotting Membranes (Bio-Rad Laboratories; Hercules, Calif.) were hybridized with probes made from the original tester and driver DNA digested with Alu I and labeled with the DIG High Prime DNA labeling kit (Roche Diagnostics Corporation, Indianapolis, Ind.). Recombinant inserts showing sequence homology to the tester DNA but not the driver DNA was selected for sequence analysis. Hybridizations were conducted on cloned inserts. At each time period, subtraction was performed, SSH 6, 10, 14, and 18. From SSH 6, 10, 14, and 18, there were 12, 29, 105, and 29 cloned inserts, respectively, that were tester specific.

The DNA sequence from each tester positive insert was determined (Lark Technologies; Houston, Tex.). Sequence from each insert was compared with sequences from the NCBI database using the blastX function. Nucleotide sequences were translated and gene function was deduced by comparing sequences to those found in the NCBI database using the blastX function. Gene function was placed in a gene category using the Clusters of Orthologous Groups (COG) web site. Specific COG genes identified were used to construct oligonucleotide probes for colony hybridization and slot-blot hybridization experiments. Four genes of the twenty-nine were selected from SSH 10 to be utilized for colony hybridization based upon functional attributes based on selection from non-acidotic cattle. The genes were selected from clones 79, 84, 94, and 110 were identified via using the NCBI blastX function with assigned functions: beta-xylosidase, glucose/galactose transporter, 4-alpha-glucanotransferase, and 4-alpha-glucanotransferase, respectively. All genes selected for colony hybridization had assigned properties as identified by COG as Carbohydrate and Transport Metabolism function, which would have provided bacteria containing these genes an advantage at metabolizing excess energy such as that found in the rumen when challenged with RFC.

Colony Hybridization:

Rumen fluid collected during the acidosis trial from cattle at times +10 h, +14 h, and +18 h was utilized. Cattle 2107, 2124, 2115, 2088, and 2133 were selected from each of these time periods. These cattle are representative of animals that were previously selected for the "tester population" or non-acidotic group. Individual rumen samples were taken from −20° C. and allowed to thaw at room temperature. Thawed rumen samples were individually plated on three separate mediums in duplicate. Media utilized consisted of sodium lactate agar (NLA), Lactate Propionibacterium Selective Agar (LPSA), and modified reinforced Clostridial media (RCS). The RCS was prepared similar to commercially available reinforced Clostridial media sans glucose. Thus, the major carbohydrate source in RCS is starch. Table 1 below indicates the incubation conditions and dilutions of rumen fluid plated on each media.

TABLE 1

Incubation conditions and dilutions plated on each media.

| | Incubation Conditions | | | |
|---|---|---|---|---|
| Media | O2 Conditions | Incubation Time | Incubation Temperature | Dilutions Plated |
| LPSA | Anaerobic | 7 Days | 32° C. | 10-1, 10-2 |
| NLA | Anaerobic | 5 Days | 37° C. | 10-2, 10-3 |
| RCS | Anaerobic | 48 Hours | 37° C. | 10-1, 10-2 |

After incubation, individual colonies were picked off of each plate and inoculated into 10 ml broth tubes consisting of the respective media, except LPSA, which was inoculated into NLB. Colonies were selected from each time period and each animal (five cattle×three time periods). For the RCS media, five colonies were picked for each animal-time period. The LPSA exhibited less colonies and diversity on the plates and number of colonies selected per animal-time period was variable. Two colonies per animal-time period were selected from the NLA media, except animal 2107 at time period 18. Six colonies were picked from this animal-time period due to increased visible diversity. Not all inoculated tubes exhibited growth after incubation.

Tubes showing growth were separated into two separate aliquots of 9 ml and 1 ml. The 1 ml aliquot was utilized for DNA isolation procedures utilizing the High Pure PCR Template Preparation Kit (Roche Molecular Biochemicals; Mannheim, Germany). The 9 ml aliquot was transferred to a sterile 15 ml Falcon Tube and centrifuged until a solid pellet was formed. The pellet was then reconstituted in NLB or RCS broths containing 10% glycerol. The reconstituted sample was placed in the −80° C. for future use. The extracted DNA was then used for RAPD-PCR analysis of individual isolates to determine phylogenic relationships. Analysis was performed using Bio-Numerics (Applied Maths Inc., Austin, Tex.) on the RAPD DNA banding patterns to determine the relatedness of the isolates. The similarity coefficient of isolates was determined using the Dice coefficient and an un-weighted pair group method (UPGMA). A similarity of 80% or greater was used to group the 109 isolates into 65 separate clusters. Of the 65 clusters, 23 grew only on RCS, 11 grew only on LPSA, 14 grew only on NLA, 4 clusters grew both on RCS and LPSA, 6 grew on both RCS and NLA, 3 grew on both LPSA and NLA, and 4 clusters were found to be present on all three media.

Slot blot hybridizations were prepared utilizing the Bio-Dot SF Microfiltration Apparatus (BIO-RAD; Hercules, Calif.). The genomic DNA of a single isolate within a cluster was selected to represent the cluster and blotted onto membranes. Probes were prepared for hybridization using the PCR DIG Probe Synthesis Kit (Roche Molecular Biochemicals; Mannheim, Germany). Probes selected were derived from the cloned insert analysis described above and consisted of four clone inserts (Clones 79, 84, 94, and 110) from SSH10. Labeled probes were pooled prior to hybridizations. Hybridizations were conducted at 45° C. for 5 hours. Colorimetric reactions were allowed to develop overnight on the membranes. Thirty of the 37 isolates (clusters) on the RCS membrane exhibited hybridization as identified by colorimetric reaction and 25 of the 28 isolates on the LPSA/NLA membrane Isolates exhibiting hybridization were then prepared for 16 s rRNA sequencing. Briefly, the 16 s rRNA of each of the 55 isolates was amplified via PCR using the primers 8F (AGAGTTTGATYMTGGCTCAG) and 1406R (ACGGGCGGTGTGTRC). The PCR product was purified using the QIAquick PCR purification kit (Qiagen, Valencia, Calif.). Purified product was analyzed by gel electrophoresis. When sufficient product was available, the purified sample was sent overnight on ice for single pass sequencing (Lark Technologies, Houston, Tex.). The 16s sequences from each cluster were compared with sequences from the NCBI database using the blastn function. Organisms of interest brought forward from this comparison consisted of *Enterococcus faecium* strain 8G-1, *Enterococcus faecium* strain 8G-73, and *Bacillus pumilus* strain 8G-134.

Example 2

In vitro Strain Testing:

Rumen fluid was collected for in vitro trials from two yearling Hereford heifers. Heifers were identified by identification tags and were referred to as 101 and 133. Heifers were fed 6 lbs/head/day of dried distillers grain (DDGS) and had access to free choice haylage.

The in vitro protocol was followed as closely as possible to decrease experimental error between each trial. Briefly, rumen fluid was collected from each heifer and placed into marked, pre-warmed thermoses. Thermoses were transported to Agtech Products, Inc. for processing. Rumen fluid was added in duplicate to bottles containing McDougall's Buffer and 3.0% glucose (final concentration after McDougall's Buffer and rumen fluid have been mixed to a volume of 180 ml), which had been tempered to 39° C. Candidate DFM strains, *Enterococcus faecium* strain 8G-1, *Enterococcus faecium* strain 8G-73, and *Bacillus pumilus* strain 8G-134, were added to designated bottles at $1.0 \times 10^7$ CFU/ml (final concentration). The unit of observation was the bottle, and treatments were performed in quadruplicate. Treatments consisted of Control (glucose added but no DFM), *Enterococcus faecium* strain 8G-1, *Enterococcus faecium* strain 8G-73, and *Bacillus pumilus* strain 8G-134. Bottles were then purged with of $CO_2$ and capped. Bottles were maintained in a shaking water bath at 39° C. and 140 rpm. Approximately 10 minutes prior to sampling, bottles were briefly vented to release gases produced as a byproduct of fermentation. Rumen fluid was withdrawn from each bottle initially and every 6 hours until the 36 hour mark. Rumen pH and volatile fatty acids were measured and recorded. Statistical analysis was performed using repeated measures analysis to determine DFM effects over time or one-way ANOVA to determine treatment affects at a specific points in time.

Figure 3:
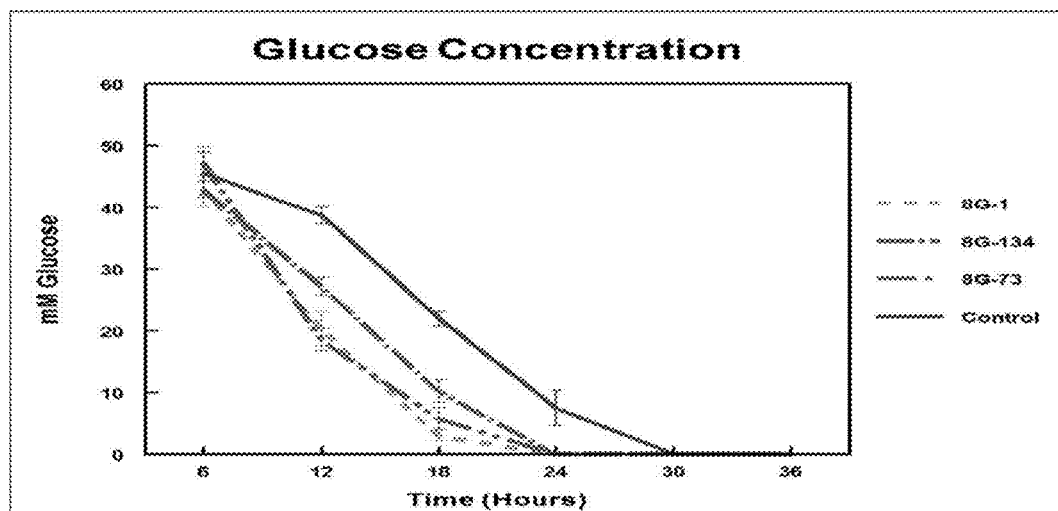
FIG. 3 is a graph showing in vitro glucose by treatment over time.
Figure 4:
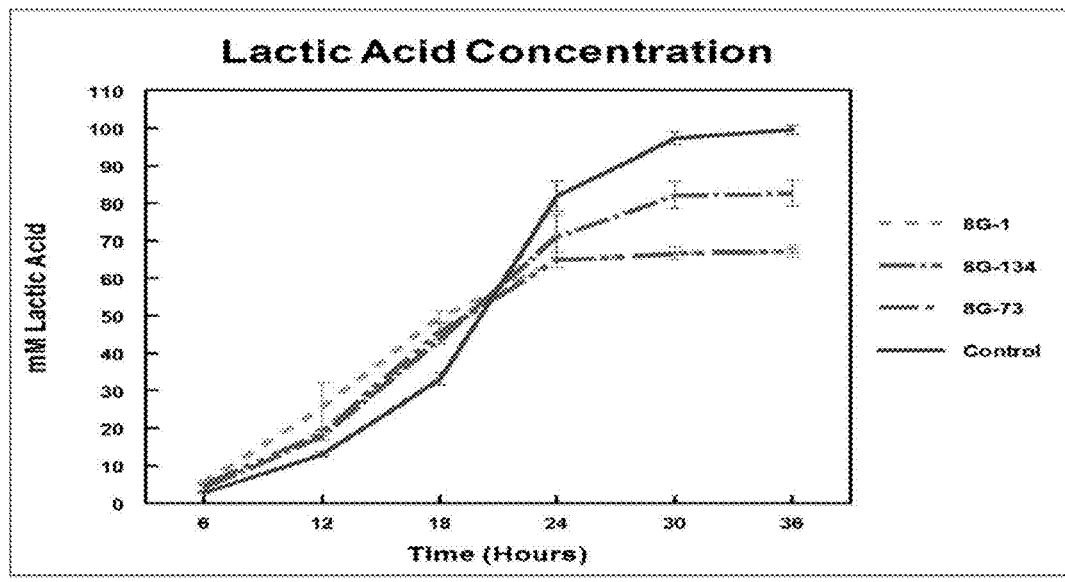
FIG. 4 is a graph showing in vitro lactic acid accumulation by treatment over time.

The focus of the ruminal in vitro experiments was to determine if candidate DFM strains, *Enterococcus faecium* strain 8G-1, *Enterococcus faecium* strain 8G-73, and *B. pumilus* strain 8G-134, could positively influence ruminal fermentation in an energy excess environment. Excess glucose was added to each ruminal in vitro, to replicate cattle engorgement with a readily fermentable carbohydrate. As shown in FIG. 3, the addition of each of the candidate strains significantly increased the utilization of glucose over time (P=0.0001). In comparison to the control (FIG. 4), the influence on lactic acid production over time was also significantly impacted by the addition of the candidate DFM to the challenged in vitro model (P=0.0025). By time point 36 hours, there was 17% less lactic acid production in the *B. pumilus* and 32% less lactic acid accumulation in both the *Enterococcus* candidates.

Figure 5:
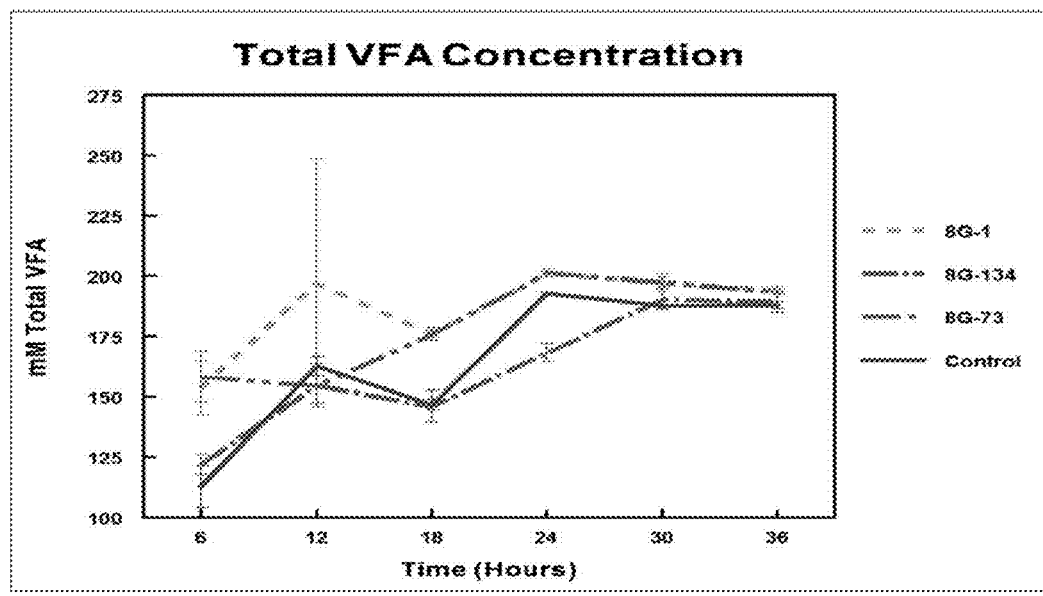
FIG. 5 is a graph showing total VFA (acetate+propionate+butyrate) accumulation over time.

Volatile fatty acid analysis was performed via HPLC. Total VFA (acetate+propionate+butyrate) were significantly affected by addition of the *Enterococcus* candidates (P=0.0279) (FIG. 5). The *Enterococcus* candidates, 8G-1 and 8G-73, appeared to increase the amount of total VFA produced over time. There was no significant effect on total VFA production when comparing the *B. pumilus* candidate to that of the control.

The in vitro results indicated that the candidate DFMs 8G-1, 8G-73, and 8G-134 positively affected ruminal fermentation by increasing glucose utilization without a corresponding increase in lactic acid production in comparison to that of the control treatment. Excess glucose in the rumen is typically fermented rapidly with the production lactic acid. It is the accumulation of lactic acid which drives an acute acidotic response. By utilizing glucose without the concomitant production of lactic acid, the candidate DFMs have demonstrated the potential to ameliorate the effects of acidosis. The ruminal in vitro model suggested that these strains may be able to successfully modulate excess ruminal energy in cattle fed high amounts of readily fermentable carbohydrates.

Example 3

Candidate DFM Testing in Cattle Fed a Readily Fermentable Carbohydrate—An Acute Acidosis Challenge:
Materials and Methods:
  Cattle and Pens Assignments:
  Twenty cross-bred beef steers were purchased at local sale barns. Cattle were housed at the research facility for a period of two weeks prior to trial initiation for observation of morbidity or mortality. Cattle were randomly blocked across treatment by weight. Five head of cattle were assigned to a pen and pens designated to one of four treatments. Treatments consisted of 3 pens each receiving a different DFM as is detailed below with the fourth pen receiving no DFM (control). Treatment assignments can be seen in Table 2 below.

TABLE 2

Treatment assignments by pen.

| Pen ID | Candidate DFM (TX) | Minimum Dose (CFU/Head/Day) | 16s rRNA Identification |
|---|---|---|---|
| 1 | None | 0 | None (Control) |
| 2 | 8G-1 | $5 \times 10^{10}$ | *Enterococcus* spp. |
| 3 | 8G-73 | $5 \times 10^{10}$ | *Enterococcus* spp. |
| 4 | 8G-134 | $5 \times 10^{9}$ | *Bacillus pumilus* |

The daily feed ration for all treatment groups prior to challenge, consisted of 62.5% roughage and 30% cracked corn and 7.5% protein supplement (Table 3) below. The protein supplement contained monensin (Rumensin®) fed at 375 mg/head/day. The protein supplement also contained tylosin phosphate (Tylan®).

TABLE 3

Challenge Ration Composition

| | Ingredient | % of Diet (DM) |
|---|---|---|
| Pre-challenge diet | Ground Hay | 62.5 |
| | Cracked Corn | 30 |
| | Steakmaker ® K+ 45-25 R500 T180* | 7.5 |
| Challenge Diet | Steam Flaked Corn | 87.4 |
| | Alfalfa Pellets | 5.1 |
| | Steakmaker ® K+ 45-25 R500 T180* | 7.5 |

*Both rations contain Rumensin and Tylan.

Cattle were fed 15 lbs/head/day of the ration once in the morning and had any remaining feed pushed closer to the feeding stanchion late in the afternoon. Fourteen days prior to fasting, treatment groups were fed candidate DFMs at the dose designated in Table 2 above as a top dressing on the daily ration.

*Bacillus pumilus* strain 8G-134 was fed at a minimum of $5 \times 10^9$ CFU/Head/Day. The *Enterococcus* candidates 8G-1 and 8G-73 were fed at $5 \times 10^{10}$ CFU/Head/Day.
Candidate DFM Preparation:
  Candidate DFM strains, previously selected for the challenge trial, were *Enterococcus* spp. 80-1 and 8G-73; and *Bacillus pumilus* strain 8G-134. Strains were stored at −80° C. Each culture was inoculated into 10 ml broth tubes containing MRS (Man, Rogosa and Sharp) or TSB (tryptic soy broth). Broth tubes were incubated for 24 hours at 32° and 37° C. for the *Bacillus* and *Enterococcus* candidates, respectively. Cultures were struck for isolation on respective agar medium and incubated. An isolated colony was picked into 10 ml of broth and allowed to grow to mid log phase (18 to 24 h) and transferred into fresh broth (10% vol/vol transfer). *Enterococcus* candidates were grown at 37° C. in MRS broth. *Bacillus* was grown at in a shaking incubator at 130 rpm at 32° C. in horizontal TSB tubes. For the growth of *Enterococcus*, 2 ml were transferred into a 250 ml bottle containing 198 ml of broth and incubated for 18 hrs.

The 200 ml of culture was inoculated into a 2 L bottle containing 1.8 L of broth and allowed to incubate for 18 hr. For the *Bacillus* candidates, 5 ml were transferred into a 250 flask containing 50 ml of TSB and then was incubated at 32° C. in a shaking incubator at 130 rpm for 24 hr. The 50 ml was used to inoculate a 1 L flask containing 600 ml and allowed to incubate for another 24 hours.

The optical density (OD) of the 18 hr culture of *Enterococcus* candidates was taken before harvesting the cells. The OD was compared to previous growth curves to determine the cfu/ml of culture. Samples were plated for enumeration and genetic fingerprinting. Quality control was ensured between each fermentation batch via RAPD-PCR analysis. With a target minimum of 5.0e10 cfu/head/day for *Enterococcus* candidates, the calculated amount of culture was dispensed into 250 ml Nalgen centrifuge bottle and spun at 4° C. for 10 min at 4500 rpm. Target minimum for *Bacillus* candidate was 5.0e9 cfu/head/day, and a total of 100 ml of the *Bacillus* culture was spun down similar to the *Enterococcus*. Supernatant was discarded. The pellet was resuspended in 30 ml of growth media containing 10% glycerol. This amount was transferred to a 50 ml conical tube. The centrifuge bottles were then rinsed with 10 ml of broth and transferred to the same conical tube. Samples were labeled with strain, date the candidate was harvested, and fermentation batch number. Plate counts were used to determine the total cfu in each tube. Tubes were combined to deliver counts of a minimum of 5.0e10 cfu/head/day for *Enterococcus* candidates and 5.0e9 cfu/head/day for *Bacillus* candidates. All conical tubes were frozen at −20° C.
Challenge Diet and Rumen Fluid Collection Phase:
  Rumen fluid samples were obtained from individual animals via ruminal intubation using a collection tube fitted with a strainer and attached to a vacuum source through a vacuum flask. The pH was immediately measured after rumen fluid acquisition and samples were frozen to be transported to Agtech Products, Inc. for VFA analysis. Samples were collected from all cattle at sample times −12 h, +6 h, +10 h, +14 h, +18 h, +22 h, +30 h, +36 h, and +48 h, with time 0 h representing the initiation of the challenge. All feed was removed from the cattle at time −24 h to initiate the fast and encourage cattle to engorge the challenge ration at time 0.

All pens were fasted for 24 hours before challenge with the concentrate diet (Time 0). The concentrate diet consisted of 28 lb flake weight steam flaked corn (Table 3 above). The challenge ration was fed to deliver 20 lbs/head. Challenge ration consumption was visually monitored and additional feed added on an as needed basis through the remainder of the trial.

Ruminal samples were collected every 4 hours from all cattle from +6 to +22 hours. Each rumen sample pH was analyzed immediately after acquisition. Rumen fluid was then frozen and transported to Agtech Products, Inc. for VFA analysis via HPLC. Repeated measures analysis was performed on rumen pH, VFAs, and glucose levels using individual animal as the unit of observation. Pairwise comparisons were performed over time between each candidate DFM treatment pens and the control pen to determine the candidates' effectiveness to alter ruminal fermentation patterns.

Results and Discussion:

Twenty head of crossbred beef cattle weighing on average 731.95 lbs were randomly blocked by weight across treatments such that there were no significant differences by weight between treatment groups (Table 4). There were 3 treatment pens and one control pen with five head/pen. Treatment assignment per pen can be seen in Table 2 above.

TABLE 4

Treatment assignments by pen.

| Pen | Treatment | N | Ave. Pen Weight in lbs (SD) | Average Feed Consumption/Steer[1] (% of Body Weight) |
|---|---|---|---|---|
| 1 | Control | 5 | 731.6 (79.94) | 4.8 |
| 2 | 8G-1 | 5 | 741.2 (94.03) | 3.9 |
| 3 | 8G-73 | 5 | 731.6 (70.12) | 3.7 |
| 4 | 8G-134 | 5 | 727.6 (72.71) | 3.6 |

[1]Average feed consumption/steer was calculated as a percentage of the average steer weight for that pen Cattle were fed challenge ration at time 0 and rumen fluid was collected at designated time points to measure ruminal fermentation values. Feed consumption per pen was monitored and recorded after 24 hours. Average feed consumption/steer was calculated as a percentage of the average steer weight for that pen (Table 4 above). The control pen (pen 1) appeared to have the highest consumption of feed in comparison to the other treatment groups with the average steer consuming 4.8% of its body weight. The lowest challenge ration consumption/pen was in pen 4 with the average steer eating approximately 3.6% of its body weight. Cattle in all pens on average would have been consuming approximately 5.625 lbs of concentrate/day as part of the pre-challenge ration, which on average would have constituted 0.8% of the average steers' body weight. Despite the pen variation of challenge ration consumption, the difference was not greater than the increase in concentrate consumption from the pre-challenge ration and would not be causative in fermentation differences between pens.

After 24 hours, feed was removed from the cattle and ground prairie hay was fed ad libitum. Cattle were given free choice hay as a precaution against the continually decreasing rumen pHs. The addition of hay would stimulate additional cud chewing and help to buffer the rumen. Despite the addition of hay, the ruminal pH still continued to decline.

Figure 6:
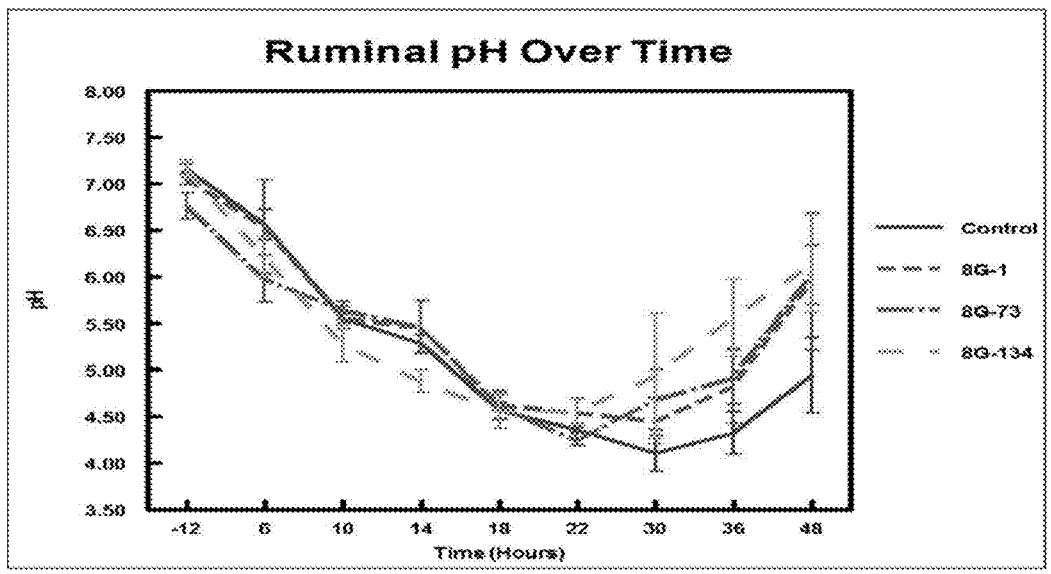
FIG. 6 is a graph showing mean ruminal pH over time in control and candidate DFM cattle.

Immediately after rumen fluid collection, sample pH was analyzed. All treatment groups exhibited a decline in ruminal pH as can be observed in FIG. 6. The pH for the control group achieved nadir at time 30 hours and began to gradually climb thereafter. By the last rumen sample collection the mean pH for the control pen was still acutely acidotic with a pH of 4.94. Acute acidosis is associated with pH that remains below 5.2 and chronic or subacute acidosis characterized by a pH below 5.6 (Owens, et. al., 1998). Mean numerically higher trends appeared for strains 8G-1, 8G-73, and 80-134 in pens 2, 3, and 4 when compared to that of the control from time +22 to +48. This suggests that cattle treated with the candidate DFMs in these pens recovered more quickly from the acidotic challenge. Mean pH for the for cattle treated with 8G-1, 80-73, and 8G-134 at time +48 was 5.96, 6.02, and 6.14, respectively, which is greater than 1.0 pH unit above the control pen. Repeated measures analysis of these three strain over time (+6 to +48) did not exhibit significant differences when compared to the control pen. However when pH comparisons of pens treated with 8G-1, 8G-73, and 8G-134 to the control pen from time +22 h to +48 h were performed, differences were or approached significance (P=0.1562, 0.0965, and 0.0466 for 8G-1, 8G-73, and 8G-134, respectively).

Figure 7:
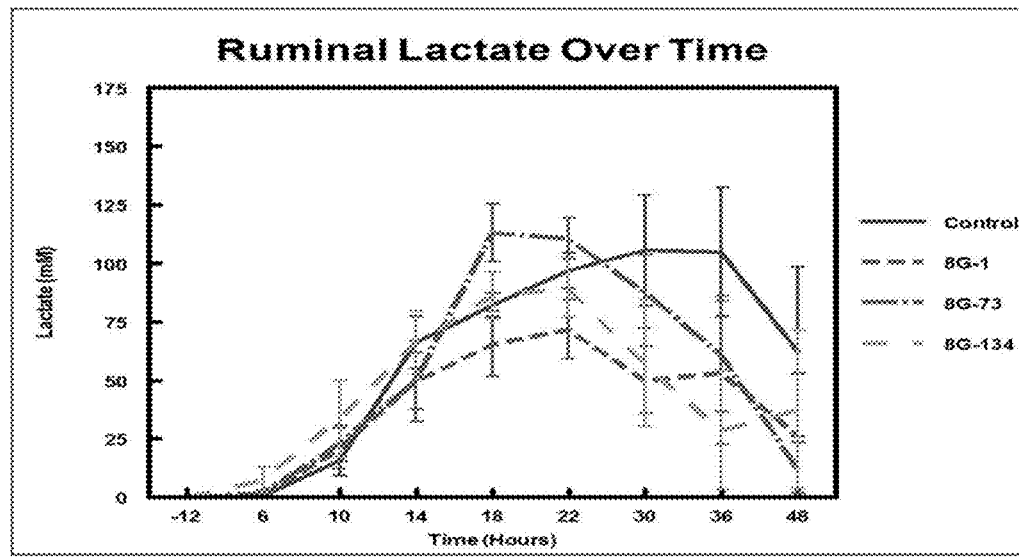
FIG. 7 is a graph showing mean ruminal lactate over time in control and candidate DFM cattle.

Average lactic acid profiles for all treatment groups are shown in FIG. 7. Mean ruminal lactic acid accumulation peaks at 105 mM for the control pen 30 hours after receiving challenge ration. Candidate DFM strains 8G-1, 8G-73, and 8G-134 again exhibited visible mean numeric differences in lactate accumulation in comparison to that of the control pen. Mean lactic acid accumulation was similar between the control cattle and the 8G-1 treated cattle through the first 14 hours of the challenge. Subsequent accumulation levels for the remainder of the trial were much less in the 8G-1 treated cattle although not significant (P=0.1892). Treatment pens 8G-73 demonstrated decreased levels of lactic acid accumulation at times 30 and remained lower than the control pen for the remainder of the trial. Candidate strain 8G-134 also showed decreased levels of lactic acid starting at +22 h and remained consistently lower than the control pen through +48 h.

Figure 8:
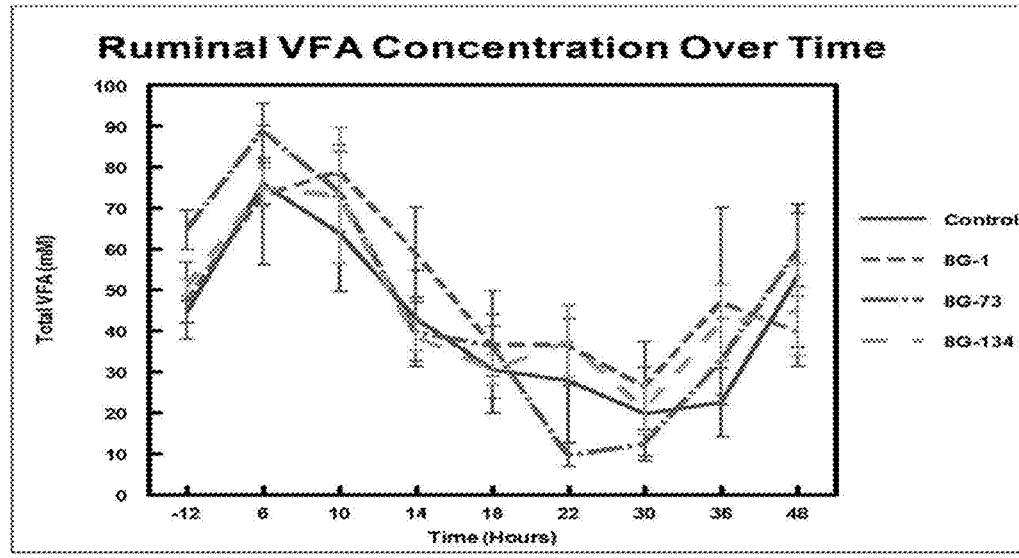
FIG. 8 is a graph showing ruminal VFA concentrations over time treatment. (Total VFA=acetate+propionate+butyrate).

Individual VFAs were measured and analyzed. Volatile fatty acid (VFA) concentrations increased in the control pen and treatments 8G-73 and 8G-134 and peaked at six hours (FIG. 8). After six hours each of these treatment pens showed declining levels of total VFA (acetate, propionate and butyrate). There were no significant differences between these treatments and the control. Treatment 8G-1, however, exhibited a delay in VFA decline which did not occur until +14 h. Over the course of the trial there were no significant differences in total VFA concentration or the individual VFA (consisting of acetate, propionate, or butyrate) levels.

In addition to monitoring and measuring ruminal fermentation characteristics over the course of the acidotic trial, cattle were observed throughout the trial for visible clinical effects associated with acidosis. Early in the acidotic challenge (+0 h to +14 h), the effects of the challenge diet were minimal. Cattle did not show signs of depression and continued to feed on the challenge ration. By +22 hours post receiving the challenge ration all cattle except those in receiving Treatment 8G-1) were showing signs of soreness, depression, and had loose, liquid fecal excretion. Cattle in pen 2 were no longer consuming feed, but did not exhibit clinical symptoms, despite similar having similarly declining pH levels.

Acute ruminal acidosis by definition is the decline in ruminal pH to levels deleterious not only to rumen function but also livestock health. Acute acidosis is marked by the accumulation of lactic acid and the decline in VFA production. Proper rumen function is a combination of managing the available energy and nitrogen components available in feedstuffs. When imbalances in ruminal metabolism occur, digestive upset typically follows and can manifest in the form acidosis. In this trial, strains 8G-1, 8G-73, and 8G-134 enhanced the recovery of rumen function as indicated by ruminal fermentation parameters.

Cattle fed 8G-1, *Enterococcus faecium*, on average recovered more quickly from the acidosis challenge as measured by pH recovery and lactic acid decline. In addition to the measured ruminal fermentation patterns, cattle fed candidate DFM 8G-1 did not exhibit clinical signs associated with acidosis.

Candidate strain 8G-73, *Enterococcus faecium*, improved ruminal fermentation through the course of the trial. Mean lactic acid levels were the lowest for all candidate strains tested at +48 h at 12.54 mM. A corresponding increase in pH was also associated with the recovery with a final pH of 6.02, which was 1.08 pH units higher than that of the control.

Candidate strain 8G-134, *Bacillus pumilus*, also enhanced ruminal recovery during the acidotic challenge. Mean lactic acid levels, in cattle fed 80-134, peaked at 89 mM at time +22 h, while the control pen continued to increase and peaked at 105 mM at time +30 hours. Mean lactic acid levels had dropped to 57 mM by +30 hours. As with lactic acid accumulation, ruminal pH in cattle fed 8G-134 recovered more quickly than that of the control and was found to be significantly different from +22 to +48 h (P=0.0466).

Example 4

Summary:

Thirty prima and multiparous Holstein cows were blocked by previous lactation and predicted producing ability (PPA) and assigned to one of three treatments. Ten cows were assigned per treatment and treatments consisted of a control group (Treatment 1) which received a basal total mixed ration (TMR), Treatment 2 and Treatment 3 which received basal total mixed ration TMR and were fed *Bacillus pumilus* 8G-134 at $5\times10^9$ and $1\times10^{10}$ CFU/head/day, respectively, from 3 weeks prepartum to 22 week after parturition. The primary objective was to determine the effects of *B. pumilus* 8G-134 on dairy cow milk production and performance above control cattle during this time period. The secondary objective was to determine if there was a dose response associated with feeding *B. pumilus* 8G-134. The *B. pumilus* 8G-134 regimens significantly increased milk production, milk fat, and decreased somatic cell count. These significant *B. pumilus* 8G-134 production effects did not come at the expense of cow body condition score, body weight, increases in dry matter intake or significantly change blood metabolite profiles, and would indicate *B. pumilus* 8G-134 also provided dairy cow efficiency benefits.

Materials and Methods:

Livestock:

Thirty Holstein cows were randomly assigned to one of three dietary treatments in a continuous lactation trial from 3 weeks prior to parturition through 22 weeks postpartum. There were no significant differences for previous milk yield for second and older cows or for predicted producing ability (PPA) for first lactation cows for the different treatment groups. The numbers of first and second lactation animals deviated between the groups, but did not influence overall mean production, as lactation was adjusted in the statistical model. Animals were on study from approximately three weeks prepartum through 22 weeks postpartum.

Nutrition:

Dietary ingredients and formulated composition of total mixed rations (TMRs) are presented in Table 5 below for dry and lactating cows, respectively. The base TMR was the same for each group and differed by top dress treatment. Each group received a top dress of 8 ounces of finely ground corn to which was added 1 ounce of maltodextrin (Treatment 1, control), *Bacillus* spp at $5\times10^9$ CFU/head/day (Treatment 2), and *Bacillus* spp at $1\times10^{10}$ CFU/head/day (Treatment 3).

TABLE 5

Formulated composition of the TMR offered to dry and lactating cows.

|  | Dry Period | Lactating Period |
|---|---|---|
| Ingredients, % DM basis |  |  |
| Corn Silage | 52.57 | 39.14 |
| Ryelage | 18.54 |  |
| Alfalfa haylage | — | 16.52 |
| Grass hay | 14.45 | 1.77 |
| SBM48 | 5.74 | 10.77 |
| Blood Meal | 4.41 |  |
| AminoPlus | — | 6.01 |
| Corn | 2.41 | 21.07 |
| Fat | 0.65 | 1.42 |
| Limestone | — | 1.26 |
| Sodium bicarbonate | — | 0.84 |
| MagOx | 0.65 | 0.42 |
| Salt | 0.32 | 0.53 |
| TMin Vit | 0.27 | 0.26 |
| Composition, % DM |  |  |
| CP | 16.50 | 16.64 |
| SP, % CP | 32.29 | 28.58 |
| NDF | 41.06 | 30.65 |
| Starch | 19.56 | 29.82 |
| Sugar | 3.19 | 2.68 |
| NFC | 33.47 | 41.87 |
| Fat | 3.82 | 4.15 |
| Ca | 0.31 | 0.87 |
| P | 0.29 | 0.34 |
| Mg | 0.54 | 0.42 |
| K | 1.72 | 1.33 |
| NeL, mcal/kg | 1.60 | 1.74 |

Sample and Data Collection:

Daily TMR samples and refusals were collected and composited weekly, weekly composites combined monthly, and monthly samples were analyzed for dry matter (DM), crude protein (CP), acid detergent fiber bound protein (ADF-CP), neutral detergent fiber bound protein (NDF-CP), soluble protein (SP), acid detergent fiber (ADF), neutral detergent fiber (NDF), lignin, fat, starch, sugar, ash, calcium (Ca), phosporus (P), magnesium (Mg), potassium (K), sulfur (S), sodium (Na), chlorine (Cl), iron (Fe), manganese (Mn), zinc (Zn), and copper (Cu) by Cumberland Valley Analytical Services, Maugansville, Md.

Cows were milked twice a day, and milk volume was recorded electronically at each milking and am-pm amounts summed for daily total. Once a week milk samples from am and pm milkings were composited for analysis of content of fat, protein, somatic cells, solids not fat, and milk urea nitrogen (MUN) by Dairy One milk laboratory in State College, Pa. using a Fossamatic 4000 (FOSS; Eden Prairie, Minn.).

Animals were on study from approximately three weeks prepartum through 22 weeks postpartum. Animal weight was estimated by heart girth circumference on weeks 1, 3, 7, 11, 15 and 18 postpartum. Body condition was assessed by two independent observers at the same time as body weight was collected.

Blood samples were collected from the coccygeal vein, serum harvested, frozen and analyzed for glucose, beta-hydroxy butyrate (BHB), and non-esterified fatty acids (NEFA) at weeks 2 and 8 postpartum. Glucose and BHB were analyzed using an Abbott Precision Xtra™ meter (Abbott Diabetes Care Inc., Alameda, Calif.). A Randox assay kit (Cat. FIN 1530, Randox Laboratories, Northern Ireland) was used to measure non-esterified fatty acid (NEFA) concentration in serum adopted to an enzyme linked immunosorbant assay (ELISA) plate reader at a wave length of 550 nm for multiple samples. The Randox kit uses Acyl CoA synthetase and oxidase to convert NEFA to 2,3-trans-Enoyl-CoA plus peroxide; peroxide plus N-ethyl-N-(2 hydroxy-3-sulphopropyl) m-toluene leads to a purple product, which is the indicator of NEFA concentration in serum.

Statistical Models.

Milk production and content, body weight, and body condition score were analyzed using the mixed procedure in SAS statistical software. Cow was the repeated subject with the covariance matrix set to type 1 correlation structure. Daily milk observations were aggregated by week postpartum. The statistical model was as follows:

$$Y_i = u_i + TRT_j + Lact_k + Week_l + TRT_j*Lact_k + TRT_j*Week_l + TRT_j*Lact_k*Week_l + e_{jklm}$$

Where
$Y_i$=least square mean of the production dependent variables;
$u_i$=overall mean of the various production variables;
$TRT_j$=jth treatment effect, 1, 2, 3;
$Lact_k$=kth lactation, 1, 2+;
$Week_l$=lth week, 1 ... 22;
interaction terms ($TRT_j*Lact_k + TRT_j*Week_l + TRT_j*Lact_k*Week_l$)
$e_{jklm}$=error Monthly samples of TMR and feed refusals for each treatment were tested for difference using means procedure in SAS.

Blood concentrations of glucose, BHB, and NEFA, were analyzed using the general linear models in SAS statistical software. Class variables were cow, week and treatment. Treatment was nested in cow and was the error term for testing treatment significance. Treatment by week interaction was tested for statistical significance using the residual error.

Results:

Mean TMR composition for dry and lactating TMRs is presented in Table 6 over the course of the study. Composition was not different between the treatment groups.

TABLE 6

Analyzed composition of TMR for dry cows and lactating cows

| | Treatment, % DM basis | | | |
|---|---|---|---|---|
| Item | 1 | 2 | 3 | SEM |
| Dry TMR | | | | |
| N | 3 | 3 | 3 | |
| CP | 13.64 | 13.17 | 13.11 | 0.14 |
| ADF | 29.55 | 28.37 | 27.88 | 0.53 |
| NDF | 48.54 | 48.04 | 47.14 | 0.93 |
| Lignin | 3.64 | 3.52 | 3.58 | 0.09 |
| Starch | 18.74 | 18.19 | 17.97 | 0.87 |
| Sugar | 6.71 | 6.15 | 6.57 | 0.23 |
| Ash | 8.44 | 7.56 | 7.79 | 0.10 |
| NFC | 39.49 | 36.93 | 38.20 | 0.86 |
| Ca | 0.49 | 0.46 | 0.47 | 0.01 |
| P | 0.37 | 0.35 | 0.35 | 0.004 |
| Lactating TMR | | | | |
| N | 9 | 9 | 9 | |
| CP, % | 14.54 | 14.81 | 14.37 | 0.10 |
| ADF, % | 21.54 | 21.38 | 21.64 | 0.25 |
| NDF, % | 33.51 | 33.21 | 33.30 | 0.32 |
| Lignin, % | 3.27 | 3.27 | 3.26 | 0.06 |
| Starch, % | 25.36 | 26.52 | 25.48 | 0.38 |
| Sugar, % | 6.25 | 6.15 | 6.25 | 0.15 |
| Fat, % | 3.69 | 3.65 | 3.62 | 0.04 |
| Ash, % | 8.73 | 8.67 | 8.60 | 0.09 |

TABLE 6-continued

Analyzed composition of TMR for dry cows and lactating cows

| | Treatment, % DM basis | | | |
|---|---|---|---|---|
| Item | 1 | 2 | 3 | SEM |
| NFC, % | 41.22 | 42.02 | 41.44 | 0.34 |
| Ca, % | 0.95 | 0.97 | 0.96 | 0.005 |
| P, % | 0.36 | 0.36 | 0.36 | 0.003 | standard error means (SEM),
NFC, nonfiber carbohydrate
NDF, neutral detergent fiber
ADF, acid detergent fiber
Treatment 1 control; Treatment 2, *Bacillus pumilus* at 8G-134 $5 \times 10^9$; Treatment 3, *Bacillus pumilus* 8G-134 at $1 \times 10^{10}$.

One control (Treatment 1) cow exhibited abnormal milk production and her data was removed from the data analysis. The analysis of milk production was repeated on 29 cows. Milk production was significantly influenced by treatment (Table 7 below). Cows fed the *Bacillus pumilus* 8G-134 at $5 \times 10^9$ CFU/head/day (Treatment 2), and *Bacillus pumilus* 8G-134 at $1 \times 10^{10}$ CFU/head/day (Treatment 3) produced significantly more milk than the cows fed the placebo control. Cows on Treatment 2 and 3 produced approximately 2 kg more milk than treatments 1 (Table 7). There was a significant interaction with parity. Production increases were significant in second parity cows by 5.2 kg, but no significant differences in milk production in first parity cows.

TABLE 7

Least square mean milk production in Holstein cows from calving through 22 weeks postpartum fed a microbial additive.

| Effect | Treatment | Lactation | Milk, kg/d | sem | Change relative to control, kg/d | sem |
|---|---|---|---|---|---|---|
| Treatment | 1 | | $33.12^a$ | 0.65 | 0.00 | 0.66 |
| Treatment | 2 | | $35.38^b$ | 0.60 | 2.30* | 0.60 |
| Treatment | 3 | | $35.08^b$ | 0.61 | 1.99* | 0.61 |
| Lactation | | 1 | $31.59^a$ | 0.47 | −0.83 | 0.47 |
| Lactation | | 2 | $36.84^b$ | 0.39 | 3.09* | 0.39 |
| Interaction | | | | | | |
| | 1 | 1 | $32.44^a$ | 1.07 | 0.00 | 1.07 |
| | 2 | 1 | $31.70^a$ | 0.93 | −0.72 | 0.93 |
| | 3 | 1 | $31.36^a$ | 0.93 | −1.07 | 0.93 |
| | 1 | 2 | $33.80^b$ | 0.74 | 0.00 | 0.74 |
| | 2 | 2 | $39.06^c$ | 0.76 | 5.24* | 0.76 |
| | 3 | 2 | $38.79^c$ | 0.79 | 5.17* | 0.79 |

Means within group with different superscript differ, $P < 0.05$
Mean change with * differ significantly from 0
Treatment 1 control; Treatment 2, *Bacillus pumilus* at 8G-134 $5 \times 10^9$; Treatment 3, *Bacillus pumilus* 8G-134 at $1 \times 10^{10}$.

Milk fat and yield are presented in Table 8 below. Milk fat was significantly increased by Treatments 2 and 3 above the control. Yield responses followed milk yield with fat yield increased in the *Bacillus pumilus* 8G-134 fed treatment groups. *Bacillus pumilus* 8G-134 cattle for treatment 2 and 3 yielded significantly higher fat percentage above that of the control with 0.24% and 0.31% higher levels, respectively (Table 8). Coupled with the significant increase in milk production, daily fat yield for both treatment 2 and 3 provided significant increases in daily fat production above that of the control (Table 8).

TABLE 8

Milk fat content by treatment groups.

| Effect | Treatment | Lactation | Fat, % | sem | Fat Yield, kg/d | sem |
|---|---|---|---|---|---|---|
| Treatment | 1 | | 3.57[a] | 0.09 | 1.206[a] | 0.042 |
| | 2 | | 3.81[b] | 0.08 | 1.351[b] | 0.039 |
| | 3 | | 3.88[b] | 0.08 | 1.351[b] | 0.039 |
| Lactation | | 1 | 3.76 | 0.06 | 1.159[a] | 0.030 |
| | | 2 | 3.78 | 0.05 | 1.395[b] | 0.025 |

Means within column with different superscript differ P < 0.05

Treatment 1 control; Treatment 2, *Bacillus pumilus* at 8G-134 5 × 10$^9$; Treatment 3, *Bacillus pumilus* 8G-134 at 1 × 10$^{10}$.

Log of the linear Somatic cell count (LogSCC) scores were different by treatment and lactation. The *Bacillus pumilus* 8G-134 treatments (Treatments 2 and 3) had significantly lower log linear score than the control cows (Table 9 below). Treatments 2 and 3 cows had LogSCC of 4.97 and 4.96, respectively compared to those of the control cows at 5.92. Parity two cows had significantly higher log linear score than first lactation cows. Somatic cell counts are associated with infection as well as immunological status and health of the lactating dairy cow. Additionally increased SCC is indicative of inflammatory responses to infection. Decreases in SCC demonstrated here may indicate that cows fed the *Bacillus pumilus* 8G-134 are better immunologically to handle infectious challenge during lactation and maintain udder and cow health.

TABLE 9

Treatment effects on Somatic Cell Count (SCC).

| Effect | Treatment | Lactation | LogSCC | sem |
|---|---|---|---|---|
| Treatment | 1 | | 5.92[a] | 0.32 |
| | 2 | | 4.97[b] | 0.30 |
| | 3 | | 4.96[b] | 0.30 |
| Lactation | | 1 | 5.27[a] | 0.23 |
| | | 2 | 5.86[b] | 0.19 |

LogScc = log of somatic cell count
Treatment 1 control; Treatment 2, *Bacillus pumilus* at 8G-134 5 × 10$^9$; Treatment 3, *Bacillus pumilus* 8G-134 at 1 × 10$^{10}$.

Data for mean DMI for groups for dry and lactating periods in Table 10 below. Dry matter intake for dry cows ranged from 10.79 to 11.64 kg/d across the groups. Lactating groups consumed 22.02, 21.31 and 21.48 kg/d for treatment groups 1, 2, and 3, respectively (Table 10). Predicted DMI based on the NRC equation for cows by week postpartum is presented in Table 10. Intake for treatment 1 was 0.83 kg higher than predicted; intake for treatment 2 was −1.37 kg lower than predicted; intake for treatment 3 was −1.04 kg lower than predicted. The increase in milk production on the Treatments 2 and 3 was accomplished with no increase in DMI. In fact the predicted or expected DMI based on NRC predictions compared to the group mean intake suggests these cows consumed 1.0 to 1.5 kg/d less DMI. Thus, the efficiency of DM utilization was increased on Treatments 2 and 3.

TABLE 10

Least square means for group feed intake, serum glucose, beta-hydroxy butyrate, non-esterified fatty acids, by treatment group.

| | Treatment group | | | | | |
|---|---|---|---|---|---|---|
| Item | 1 | sem | 2 | sem | 3 | sem |
| Dry Matter Intake, kg/d | | | | | | |
| Dry cows | 10.79 | 0.27 | 11.64 | 0.25 | 11.12 | 0.25 |
| Lactating cows | 22.02 | 0.11 | 21.31 | 0.11 | 21.48 | 0.11 |
| Predicted DMI, kg/d | 21.19 | 0.58 | 22.68 | 0.57 | 22.52 | 0.58 |
| Serum values | | | | | | |
| Glucose, mg/dl | 53.95 | 1.98 | 51.5 | 1.98 | 53.5 | 1.98 |
| Beta-OH butyrate, mg/dl | 1.05 | 0.15 | 0.88 | 0.15 | 1.15 | 0.15 |
| NEFA, ueq/ml | 0.23 | 0.04 | 0.16 | 0.04 | 0.17 | 0.04 |
| Serum values by week, 2, 8; | | | | | | |
| Glucose, mg/dl | 52.90 | 2.80 | 47.00 | 2.80 | 48.90 | 2.80 |
| | 55.00 | 2.80 | 56.00 | 2.80 | 58.10 | 2.80 |
| BHB, mg/dl | 0.92 | 0.21 | 0.86 | 0.21 | 1.39 | 0.21 |
| | 1.17 | 0.21 | 0.89 | 0.21 | 0.91 | 0.21 |
| NEFA, ueq/ml | 0.41 | 0.05 | 0.23 | 0.05 | 0.28 | 0.05 |
| | 0.07 | 0.05 | 0.10 | 0.05 | 0.07 | 0.05 |

BHB = beta-hydroxy butyrate
Treatment 1 control; Treatment 2, *Bacillus pumilus* at 8G-134 5 × 10$^9$; Treatment 3, *Bacillus pumilus* 8G-134 at 1 × 10$^{10}$.
Predicted DMI = (.372 * FCM + 0.0968 * BWT(kg)$^{.75}$) * (1 − exp(−0.192 * (Week + 3.67)))

The DMI differences and production values could suggest that cows on Treatments 2 and 3 could have mobilized more body tissue than the control cows to produce more milk and eat less than expected. However, serum NEFA, glucose, and BHB suggest these cows were in similar energy status as control cows (Table 10 above). Additionally, body weight and BCS were similar for the *Bacillus* groups relative to the control group (Table 11 below). This suggests they did not mobilize more body tissue to produce the additional milk volume, indicating feed conversion efficiency in cows feed Treatments 2 and 3 regardless of dose.

TABLE 11

Least square mean body weight (lb) and body condition score by treatment groups.
Body condition score is the average score of two observers.

| Effect | Treatment | Lactation (lb) | Wt, | sem | BCS | sem |
|---|---|---|---|---|---|---|
| Treatment | 1 | | 1343.10 | 28.49 | 2.92 | 0.03 |
| | 2 | | 1324.60 | 27.54 | 3.13 | 0.03 |
| | 3 | | 1388.02 | 27.73 | 3.06 | 0.03 |
| Lactation | | 1 | 1223.31 | 21.87 | 3.04 | 0.02 |
| Lactation | | 2 | 1476.62 | 17.94 | 3.01 | 0.02 |
| Interaction Treatment × lactation | | | | | | |
| 1 | 1 | | 1170.78 | 27.72 | 3.06 | 0.05 |
| 2 | 1 | | 1242.64 | 25.26 | 3.17 | 0.05 |
| 3 | 1 | | 1208.50 | 24.00 | 2.94 | 0.05 |
| 1 | 2 | | 1486.02 | 19.33 | 2.78 | 0.04 |
| 2 | 2 | | 1406.42 | 19.96 | 3.10 | 0.04 |
| 3 | 2 | | 1547.85 | 20.79 | 3.19 | 0.04 |

Wt = weight, lbs
BCS = body condition score, scale 1 to 5 by 0.25 points; 1 = emaciated, 2 = thin, 3 = average, 4 = fat, 5 = obese
Treatment 1 control; Treatment 2, *Bacillus pumilus* at 8G-134 5 × 10$^9$; Treatment 3, *Bacillus pumilus* 8G-134 at 1 × 10$^{10}$.

Example 5

Materials and Methods

A. Study Design

Forty-eight (n=12/treatment) multiparous Holstein and Holstein cross (Holstein×Montbéliarde×Swedish Red) dairy cows were blocked by lactation, BCS, and body weight, and randomly assigned to a 2×2 factorial design (pre- and postpartum starch [low vs. high] and supplementation of either an inert limestone carrier or BP+carrier postpartum). Factors combined resulted in 4 treatments: (1) LS pre and postpartum+inert limestone carrier postpartum (LSCO); (2) LS pre and postpartum+*Bacillus pumilus* 8G-134 (BP) postpartum (LSBP); (3) HS pre and postpartum+inert limestone carrier postpartum (HSCO); (4) HS pre and postpartum+BP postpartum (HSBP). *Bacillus pumilus* was added by top dressing 28 g/d of powder product on the TMR once daily to provide $5 \times 10^9$ colony-forming units (CFU)/head per day of live BP strain (DuPont Nutrition and Health, Waukesha, Wis.) from calving to 112 DIM.

B. Blood Collection and Analyses

Blood samples were collected weekly on d −28, −21, −14, −7, 1, 7, 14, 21, 28 relative to calving at 0800 h. Approximately 10 mL of blood was collected from the coccygeal vein into an evacuated serum tube (serum separator, Becton Dickinson Vacutainer systems, Franklin Lakes, N.J.), centrifuged at 2,000×g for 20 min immediately after sample collection, and frozen at −20° C. until analysis. Serum NEFA concentrations were determined using a NEFA C kit (Wako Diagnostic, Richmond, Va.). Serum glucose concentrations were quantified by enzymatic reaction (Stanbio Laboratory, Boerne, Tex.). Serum calcium concentrations on d −7 and d 1 relative to calving were measured using a calcium (Arsenazo) reagent set (Point Scientific, Inc., Canton, Mich.). Serum haptoglobin concentrations were determined by a colorimetric procedure as described by Hulbert et al. (2011). Absorbance for NEFA, glucose, calcium, and haptoglobin assays was quantified using a microplate spectrophotometer (Eon TM, BioTek Instruments Inc., Winooski, Vt.). Serum BHBA concentrations were quantified using the Precision Xtra® ketone monitoring system direct electrochemical test (Abbot Laboratories Inc., Abbott Park, Ill.). Briefly, a droplet of serum was placed on a ketone test strip containing the enzyme β-hydroxybutyrate dehydrogenase, which oxidizes BHBA to acetoacetate. The enzyme β-hydroxybutyrate dehydrogenase reduces nicotinamide adenine dinucleotide (NAD+) to NADH. The NADH is then reoxidized to NAD+ by an electron transfer mediator molecule. The electrical current generated by this conversion is measured by the meter and is directly proportional to the BHBA concentration (Oetzel and McGuirk, 2007).

C. Statistical Analysis

Data were analyzed using SAS (version 9.2 SAS Institute, Cary, N.C.). Prepartum and postpartum data were analyzed separately. Prepartum data were analyzed as a completely randomized design using MIXED models procedures of SAS. Model included effects of breed, starch concentration, time and interaction of starch concentration by time.

Postpartum data were analyzed as a randomized complete block design with a 2×2 factorial arrangement of treatments using MIXED models procedure of SAS. Model included effects of breed, starch concentration, BP, time, and interactions between starch, BP, and time. On pre- and postpartum periods repeated measures over time were modeled with autoregressive [AR (1)], and denominator degrees of freedom were estimated using Kenwards-Rogers method. Single measurements were modeled with autoregressive [AR (1)], and denominator degrees of freedom were estimated using Satterthwaite methods. Least squares means for starch, BP, time and all interactions were separated by use of PDIFF statement when the overall F-test was P≤0.05. Trends were indicated when P≤0.10.

Results: Feeding *B. pumilus* 8G-134 Reduces the Levels of Nonesterified Fatty Acids (NEFA) in the Blood of Dairy Cows in the Early Postpartum Period Blood serum concentrations of glucose, beta-hydroxybutyrate (BHBA), and nonesterified fatty acids (NEFA) are considered to be good indicators of a cow's energy balance. Higher blood NEFA and beta-hydroxybutyrate (BHBA) are typical in the early postpartum period when cows are partitioning energy toward milk production, and are known to be negatively correlated with energy balance.

Figure 9:
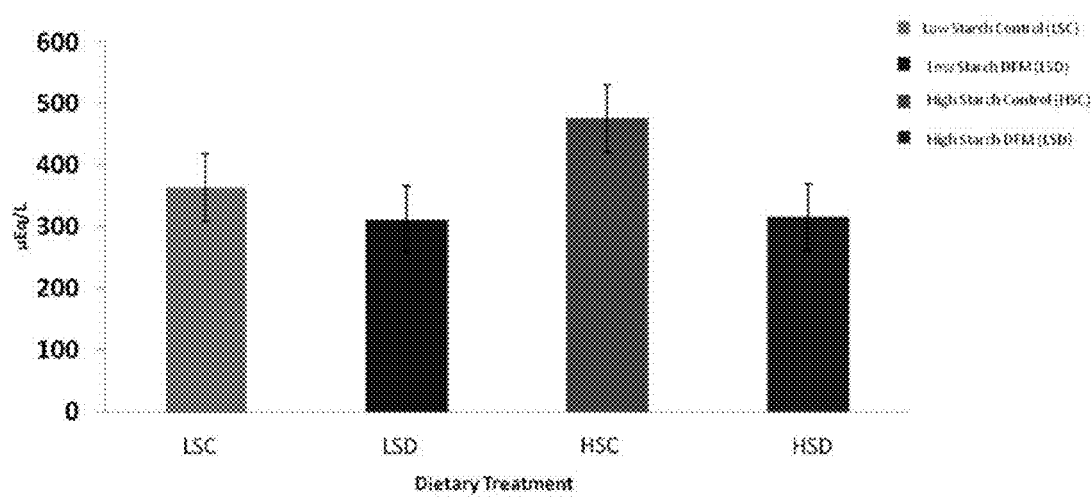
FIG. 9 is a bar graph depicting postpartum NEFA levels in the blood of dairy cows. Levels are means of day 7, 14, 21 and 28 day postpartum measurements. DFM treatments were administered *B. pumilus* 8G-134 at $5 \times 10^9$ CFU/cow/day. Effects of DFM treatment (P=0.05) and day (P<0.0001) were significant.

Multiparous cows fed *B. pumilus* 8G-134 at $5 \times 10^9$ CFU/cow/day showed an improvement in blood NEFA during early lactation, with no detrimental impact on milk production when cows were fed a high starch diet (Table 12, FIG. 9). A numerical reduction in postpartum NEFA was also observed for cows fed a low starch diet. Nutrient composition of diets is shown in Table 13.

TABLE 12

Least square mean comparison of early postpartum NEFA measured on d. 7, 14, 21, and 28 postpartum

|  | Low Starch Control | Low Starch with DFM | High Starch Control | High Starch with DFM | SEM |
|---|---|---|---|---|---|
| NEFA (μEq/L) | 364$^{ab}$ | 312$^b$ | 476$^a$ | 315$^b$ | 69 |

TABLE 13

Nutrient composition of high and low starch diets

| | Prepartum | | Postpartum | |
|---|---|---|---|---|
| Variable | Low starch | High Starch | Low Starch | High Starch |
| DM, % | 54 | 54 | 54 | 54 |
| CP, % | 17.6 | 17.6 | 17.5 | 17.6 |
| RUP (% CP) | 31.8 | 33.5 | 41 | 43.1 |
| RDP (% CP) | 68.2 | 66.5 | 59 | 57 |
| ADF, % | 26.9 | 24 | 18.5 | 15.2 |
| NDF, % | 46.3 | 41.6 | 32.5 | 27.4 |
| NE$_L$, Mcal/kg | 1.85 | 1.9 | 2.4 | 2.5 |
| Starch, % | 14 | 20.3 | 23.8 | 30.4 |
| Sugar, % | 5 | 5.1 | 5.7 | 5.9 |
| Fat, % | 3.1 | 3.3 | 3.3 | 3.5 |
| Ash, % | 9.3 | 9.6 | 8.3 | 8.7 |

DM = dry matter,
CP = crude protein,
RUP = rumen undegradable protein,
ADF = acid detergent fiber,
NDF = neutral detergent fiber,
NE = net energy

Example 6

Overview

At calving and during early lactation, many high producing dairy cows are unable to consume enough feed to meet energy demands, resulting in a state of negative energy balance. Energy balance (EB), quantified using measures of milk production (quantity and composition), dietary intake (quantity and composition), and body condition, has been associated with postpartum health and fertility. Often during a state of negative energy balance, high milk production can come at the expense of body condition score, as fat and muscle are mobilized to support production, particularly in high yielding dairy cows. Loss of body condition is associated with altered blood metabolite and hormone profiles which may influence fertility and it has been demonstrated that cows with a low body condition score at 7-10 weeks postpartum take longer to conceive. In addition, negative energy balance is associated with metabolic diseases such as ketosis. During ketosis there is an accumulation of beta-hydroxybutyrate (BHBA) and other ketone bodies in the blood (5), and clinical and subclinical ketosis have been shown to significantly reduce milk yield in dairy herds by approximately 1-1.5 kg milk/day (5, 9).

Influencing the energy partitioned between milk and body tissue is one strategy to balance milk production, health, and reproductive efficiency. Blood serum concentrations of glucose, beta-hydroxybutyrate (BHBA), and nonesterified fatty acids (NEFA) are considered to be good indicators of a cow's energy balance. Data presented below use NEFA, BHBA, disease incidence metrics and immune data to support the use of *B. pumilus* 8G-134 to improve energy balance. It is likely that *B. pumilus* 8G-134 is influencing the energy balance of dairy cows through an immunomodulatory mechanism, having downstream beneficial impacts on metabolic markers (including NEFA and BHBA), metabolic diseases (SCK and RP), and eventually milk production. It is anticipated that greater reproductive efficiency will also be a result of *B. pumilus* 8G-134 administration.

Materials and Methods

A. Animal Care and Housing

All experimental procedures were approved by the University of Illinois at Urbana-Champaign Institutional Animal Care and Use Committee. Forty-three multiparous Holstein cows were assigned to two treatments in a randomized complete block design. During the prepartum period, cows were housed in free stalls with individual Calan feed gates (American Calan Inc., Northwood, N.H.). Approximately 2 d before expected parturition, cows were moved to individual maternity pens in the same barn until parturition. After parturition, cows were housed in tie stalls with mangers designed for measurement of feed intake. Cows were milked three times daily. During the experimental period, cows were fed for ad libitum intake. Diets (pre- and postpartum) were formulated to meet or exceed cows' requirements according to NRC (2001) and were delivered once daily as a total mixed ration (TMR).

B. Treatments and Management

Cows in the DFM treatment (DFMt, n=21) received $5.0 \times 10^9$ cfu/cow of *Bacillus pumilus* 8G-134 DFM (DuPont Nutrition and Health, Waukesha, Wis.) in 28 g of maltodextrin carrier, whereas cows in the control treatment (CON, n=22) received 28 g of maltodextrin carrier alone as a placebo. Treatments were mixed with 0.45 kg ground corn and top-dressed on the close-up or lactation TMR once daily for each cow. Treatments were applied from 21±1 d before expected calving date to 154 d after calving. Cows were randomly assigned to treatments and balanced for initial body weight (BW; 719±9.59 kg vs 715±9.78 kg for CON and DFMt, respectively), parity (2.53±0.42 vs 2.03±0.36 for CON and DFMt, respectively), and previous lactation (305 d) milk production (11,703±543 kg vs 11,389±473 kg for CON and DFMt, respectively).

C. Sample Collection

Feed ingredients and TMR samples were obtained weekly and analyzed for dry matter (DM) content (AOAC, 1995) by drying for 24 h in a forced-air oven at 110° C. Dietary DM was adjusted weekly for changes in DM content. Total mixed ration samples were taken weekly, and stored at −20° C. until submitted for analysis. Monthly composite samples were analyzed for contents of DM, crude protein (CP), acid-detergent fiber (ADF), neutral-detergent fiber (NDF), lignin, starch, fat, ash, Ca, P, Mg, K, Na, Fe, Zn, Cu, Mn, Mo, and S using wet chemistry methods (Dairy One, Ithaca, N.Y.). Values for RFV, TDN, NE1, NEm, NEg, ME, and DE were provided by the lab and were based on NRC (2001). Intake from each cow was measured and DMI was recorded daily.

Cows were milked 3 times daily at 0600, 1400, and 2100 h. Milk weights were recorded daily and samples were obtained from 3 consecutive milkings weekly. Consecutive weekly samples were composited in proportion to milk yield at each sampling and preserved (800 Broad Spectrum Microtabs II; D&F Control Systems, Inc., San Ramon, Calif.). Composite milk samples were analyzed for fat, protein, lactose, urea N (MUN), total solid and somatic cell count (SCC) using mid-infrared procedures (AOAC, 1995) at a commercial laboratory (Dairy Lab Services, Dubuque, Iowa).

Health disorders included retained placenta (RP), displaced abomasum (DA), clinical ketosis (CK), mastitis (MAST), and metritis (MET). Retained placenta was defined as placenta that failed to deliver completely longer than 12 h after calf delivery; DA was diagnosed by a veterinarian; CK was diagnosed by urinalysis strip (Ketostix, Bayer Corp. Diagnostics Division, Elkhart, Ind.); MAST was diagnosed by altered milk composition confirmed by positive microbiological culture; and MET was defined as uterine discharge that is foul, purulent, orange-brown in color. Fecal score (FS) and general appearance (GA) were recorded daily. Fecal scores were on a 1 to 4 scale according to (Krause et al., 2009): 1=runny: liquid consistency, splatters on impact, spreads readily; 2=loose: may pile slightly and spreads and splatters moderately on impact and setting; 3=soft: firm but not hard, piles but spreads slightly on impact and settling; 4=dry: hard, dry appearance, original form not distorted on impact and settling. General appearance was scored as (Krause et al., 2009): 1: bright and alert; 2: depressed; 3: reluctant to rise. Cows with fecal score≤2 were classified as experiencing transient digestive problems (FS ≤2) whereas cows with FS>2 were classified as healthy (HEALTHY). Cows with GA≥2 were classified as sick (ALTERED) whereas cows with GA<2 were classified as healthy (HEALTHY).

Body weight was measured and body condition score (BCS) was assigned in quarter unit increments (Ferguson et al., 1994) for each cow weekly. More than one individual assigned BCS independently at each time of scoring throughout the experiment.

Blood samples were collected from the coccygeal vein or artery on d 5 and d 14 after calving. Beta-hydroxybutyrate (BHBA) was measured immediately after the collection with a commercial blood ketone monitoring system (Precision Xtra, Abbott Diabetes Care Inc., Alameda, Calif.). Cows that had blood BHBA concentrations higher than 1.2 mmol/L were classified as experiencing sub-clinical ketosis (SCK). Blood samples were collected into tubes (BD Vacutainer; BD and Co., Franklin Lakes, N.J.) containing clot activator for serum. Serum samples were obtained by centrifugation at 1,300×g for 15 min and stored at −20° C. until analyzed. Serum samples were analyzed for non-esterified fatty acids (NEFA), which was determined by enzymatic analysis (NEFA-HR(2), Wako Diagnostics, Richmond, Va.). Cows that had NEFA serum concentrations higher than 0.7 mEq/L were classified as high (HNEFA) whereas cows that had NEFA serum concentrations lower than 0.7 mEq/L were classified as low (LNEFA). Both BHBA and NEFA variables were dichotomized based on cut-off points previously established by Ospina et al. (2010). The immunoglubulins, IgA, IgG and IgM were quantified in milk collected during the first week after calving and serum collected on d 5 and d 14 by an ELISA assay (Bethyl laboratories, Montgomery, Tex.) according to the manufacturer's protocol. Haptoglobin was quantified in serum samples by an ELISA assay (ALPCO, SALEM, N.H.) according to the manufacturer's protocol. Cows that had haptoglobin serum concentrations lower than 20 μg/ml were classified as negative (NEGATIVE) whereas cows that had serum haptoglobin concentrations higher than 20 μg/ml were classified as positive (POSITIVE), according to cut-off points previously established by Eckersall et al. (2010).

D. Statistical Analyses

The data were analyzed using SAS (v 9.3; SAS Institute Inc., Cary, N.C.). The MIXED models procedure was used for the outcomes of interest DMI, BW, BCS, milk parameters, and composed variables (e.g. FE), which were averaged weekly. The model contained the fixed effects of treatment, week, and the interaction of treatment by week. Initial measurements, before treatment administration, were used as covariates when analyzing the dependent variables BW and BCS. Variables were subjected to 5 covariance structures: compound symmetry, autoregressive order 1, autoregressive heterogeneous order 1, unstructured, and Toeplitz. The covariance structure that yielded the lowest corrected Akaike information criterion was used in the model (Littell et al., 1998). Cow was the experimental unit and considered as a random effect. Week was included in the model as a repeated measurement with cow as subject. All performance variables were analyzed as weekly averages. Least squares means were calculated and are presented with standard errors of means (SEM). Degrees of freedom were estimated by using the Kenward-Roger method in the model statement (Littell et al., 1998). Residual distribution was evaluated for normality and homoscedasticity.

Dry matter intake change from 3 wk before and after calving, milk yield change from calving to 3 wk, blood BHBA, plasma NEFA, serum and milk IgA, Ig M, IgG and serum haptoglobin concentrations were analyzed as continuous variables using the MIXED procedure. A multivariable logistic mixed models (GLIMMIX procedure) was used for the dichotomized variables (SCK, NEFA, RP, DA, CK, MET, MAST, FS, GA, and HAPTOGLOBIN). The procedure used for each variable is also indicated in the results section for each outcome of interest. A log transformation was used for the variables NEFA, SCC, and haptoglobin for better homogeneity of the distribution of residuals. Means shown in tables and graphs for these variables are back-transformed. Statistical significant declared as P value lower than 0.05, and tendency declared as P value lower than 0.10.

Results

A. Feeding *B. pumilus* 8G-134 Reduces Disease Associated With Negative Energy Balance in Early Postpartum Dairy Cows.

Multiparous dairy cows fed *B. pumilus* 8G-134 at $5 \times 10^9$ CFU/cow/day had a tendency for lower incidence of subclinical ketosis (SCK) at d 5 postpartum (P=0.09) as measured by blood BHBA level than cows fed a control diet with no DFM (Table 14). Cows fed *B. pumilus* 80-134 at $5 \times 10^9$ CFU/cow/day also tended (P=0.13) to have lower incidence of retained placenta (RP) than cows fed a control diet with no DFM (Table 15).

TABLE 14

Comparison of the incidence of early postpartum subclinical ketosis

|  | Control | DFM |
|---|---|---|
| Incidence (# cows) with SCK (BHBA ≥ 1.2 mmol/L) | 8 | 5 |
| Incidence (# cows) with no SCK (BHBA ≤ 1.2 mmol/L) | 6 | 13 |

Chi Square, P = 0.09.
DFM = *B. pumilus* 8G-134 at $5 \times 10^9$ CFU/cow/day

TABLE 15

Comparison of the incidence of retained placenta

|  | Control | DFM |
|---|---|---|
| Incidence (# cows) with retained placenta (RP) | 2 | 0 |
| Incidence (# cows) with no retained placenta (RP) | 17 | 20 |

Chi Square, P = 0.13.
DFM = *B. pumilus* 8G-134 at $5 \times 10^9$ CFU/cow/day

B. Multivariable Logistic Mixed Models of Blood Metabolites and Health Occurrences From Holstein Cows Top-Dressed With *Bacillus pumilus* 8G-134 (DFMt) or Placebo (CON) From Week 4 Before Calving Through Week 22 After Calving At 14 DIM there was a tendency (P=0.07) for cows receiving CON having greater odds (OR=3.21) of being classified as HNEFA when compared to DFMt cows (Table 16). At 5 DIM there was a tendency (P=0.06) for cows receiving CON having greater odds (OR=3.85) of being classified as SCK when compared to DFMt cows (Table 16). There was no difference (P>0.18) detected on blood haptoglobin concentration between treatments on either d 5 or d 14. There was a tendency (P=0.09) for cows receiving CON to have greater odds (OR=3.55) of being classified as POSITIVE when compared to DFMt cows at d 14 after calving (Table 14).

There were no differences (P>0.25) in the concentration of IgG and IgM in milk or serum samples. Milk concentrations of IgA were higher (P=0.03) during the first week from DFMt cows when compared to CON, however, there was no difference (P=0.42) in serum IgA concentrations between treatments. In regard to serum haptoglobin, at 14 DIM there was a tendency (P=0.09) for cows receiving CON to have greater odds (OR=3.55) of being classified as POSITIVE when compared to DFMt cows (Table 16).

Cows that received CON showed signs of excessive adipose tissue mobilization as indicated by higher levels of BHBA and NEFA after calving when compared to DFMt cows (Table 16). DFMt improved immunity in the mammary gland and reduced the incidence of an elevated haptoglobin response. All the measured health occurrences are shown in Table 16. When analyzed for its frequency, cows receiving CON tended (P=0.08) to have higher probability of digestive occurrence when compared to DFM cows (Table 16).

TABLE 16

Multivariable logistic mixed models of blood metabolites and health occurrences from Holstein cows top-dressed with *Bacillus pumilus* 8G-134 (DFMt) or placebo (CON) from week 4 before calving through week 22 after calving.

| Variable | DRC[1] | n[2] | TRT diff.[3] | Level | Coefficient | SEM | Odds Ratio | 95% CI[4] | P-value |
|---|---|---|---|---|---|---|---|---|---|
| Blood | | | | | | | | | |
| NEFA, mEq/L | 5 | 37 | CON − DFM | HNEFA | −0.6061 | 0.67 | 0.54 | 0.14-2.05 | 0.37 |
|  | 14 | 42 | CON − DFM | HNEFA | 1.1675 | 0.64 | 3.21 | 0.91-11.4 | 0.07 |
| BHBA, mmol/L | 5 | 37 | CON − DFM | SCK | 1.3499 | 0.72 | 3.85 | 0.94-15.8 | 0.06 |
|  | 14 | 42 | CON − DFM | SCK | −0.1053 | 0.62 | 0.90 | 0.26-3.07 | 0.86 |
| Haptoglobin, μg/ml | 5 | 37 | CON − DFM | Positive | 0.5523 | 0.57 | 1.73 | 0.55-5.53 | 0.34 |
|  | 14 | 42 | CON − DFM | Positive | 1.2692 | 0.75 | 3.55 | 0.78-16.19 | 0.09 |
| Health occurrences | | | | | | | | | |
| RP[5] | | 43 | CON − DFM | Yes | 10.8448 | 148.8 | >99 | — | 0.94 |
| DA[6] | | 43 | CON − DFM | Yes | 0.05407 | 0.88 | 1.05 | 0.19-5.92 | 0.95 |
| CK[7] | | 43 | CON − DFM | Yes | 0.05407 | 0.88 | 1.05 | 0.18-5.91 | 0.95 |
| MAST[8] | | 43 | CON − DFM | — | — | — | — | — | — |
| MET[9] | | 43 | CON − DFM | — | — | — | — | — | — |
| FS[10] | | 5945 | CON − DFM | FS ≤ 2 | 0.02971 | 0.0175 | 1.03 | 0.99-1.07 | 0.08 |
| GA[11] | | 5945 | CON − DFM | Altered | −0.00063 | 0.03 | 0.99 | 0.95-1.06 | 0.98 |

[1] Days relative to calving.
[2] Observations used from both CON and DFM treatments.
[3] Differences of treatment least squares means.
[4] 95% confidence interval.
[5] RP: Retained placenta; CON (n = 21; YES = 2, and NO = 19) and DFM (n = 22; YES = 0, and NO = 22).
[6] DA: Displacement of abomasum; CON (n = 21; YES = 3, and NO = 18) and DFM (n = 22; YES = 3, and NO = 19).
[7] CK: Clinical Ketosis; CON (n = 21; YES = 3, and NO = 18) and DFM (n = 22; YES = 3, and NO = 19).
[8] MAST: Mastitis; CON (n = 21; YES = 0, and NO = 21) and DFM (n = 22; YES = 0, and NO = 22).
[9] MET: Metritis; CON (n = 21; YES = 0, and NO = 21) and DFM (n = 22; YES = 0, and NO = 22).
[10] FS: Fecal score: 1 = runny; 2 = loose; 3 = soft; 4 = dry; CON (n = 2920; "FS ≤ 2"= 123, and HEALTHY = 2797) and DFM (n = 3024; "FS ≤ 2", and HEALTHY = 2951). No time (P = 1.00) or treatment by time (P = 1.00) effect observed.
[11] GA: General appearance: 1: Bright and alert; 2: Depressed; 3: Reluctant to rise. CON (n = 2920; Altered = 27, and HEALTHY = 2893) and DFM (n = 3024; Altered = 27, and HEALTHY = 2997). No time (P = 1.00) or treatment by time (P = 1.00) effect observed. NEFA classes based on: serum concentrations ≤ 0.7 mEq/L (LNEFA; referent); and high > 0.7 mEq/L (HNEFA). BHBA classes based on: blood concentrations ≤ 1.2 mmol/L (SCK = NO; referent); and high > 1.2 mmol/L (SCK = YES). Haptoglobin classes based on: serum concentrations ≤ 150 μg/ml (Haptoglobin = NEGATIVE, referent); and positive > 150 μg/ml (Haptoglobin = POSITIVE D. Milk Yield of Holstein Cows Top-Dressed with *Bacillus pumilus* 8G-134 (DFMt)

Upon administration of *Bacillus pumilus* 8G-134, milk production was maintained while NEFA were lower (see data above and Table 17). Typically, when lower NEFA are observed, a lower milk yield is also observed, which is undesirable. In this case, the milk yield was maintained while the NEFA levels were lowered, which indicates that the treated cows do not need to mobilize body fat resources to the same extent as the control animals in order to produce the same volume of milk—an energy savings as well as a health benefit.

TABLE 17

Milk parameters response (least squares means) of Holstein cows top-dressed with *Bacillus pumilus* 8G-134 (DFMt) or placebo (CON) from wk 4 before calving through wk 22 after calving.

| | Treatment | | | P-value | | |
|---|---|---|---|---|---|---|
| | CON | DFM | SEM | Trt | Week | Week × Trt |
| Milk yield, kg/d | 41.6 | 42.2 | 0.88 | 0.61 | <0.01 | <0.01 |

E. IgA in Milk of Holstein Cows Top-Dressed With *Bacillus pumilus* 8G-134 (DFMt) Immunoglobulin A Have Protective Effects That Would Aid in the Defense Against Pathogens in the Mammary Gland.

Milk concentrations of IgA was higher from DFMt cows when compared to CON (see Table 18). Immunoglobulin A, normally found at mucosal sites, binds to bacterial cells and prevents their adhesion to epithelial cells. The additional immune defense provided by DFMt could explain the difference in haptoglobin levels between DFMt and CON cows. In a healthy cow, serum haptoglobin concentration is below 20 μg/ml. In response to disease such as mastitis or endometritis, haptoglobin serum concentrations can increase 100 fold or more. An increase in IgA in the mammary gland may provide greater protection against infection, reducing the incidence of disease and elevated haptoglobin concentrations, Elevated milk immunoglobulins also have the added benefit of boosting neonatal calf health through passive transfer of immunity. IgA in particular provides mucosal protection in the calf gastrointestinal tract, aiding in the development of a healthy immune system and gut microbiota.

TABLE 18

Least squares means of IgA in milk from Holstein cows top-dressed with *Bacillus pumilus* 8G-134 (DFM) or placebo (CON) from wk 4 before calving through wk 22 after calving at 5 and 14 d relative to calving.

| | | Treatment | | | |
|---|---|---|---|---|---|
| Variable | n[1] | CON | DFM | SEM | Trt |
| Milk[2] | | | | | |
| IgA, μg/ml | 40 | 478 | 584 | 35.0 | 0.03 |
| IgG, μg/ml | 40 | 514 | 512 | 65.0 | 0.99 |
| IgM, μg/ml | 40 | 6.94 | 8.02 | 0.90 | 0.40 |

[1] Observations used from both CON and DFM treatments..
[2] Sample collected on the first week of lactation.

Example 7

Figure 10:
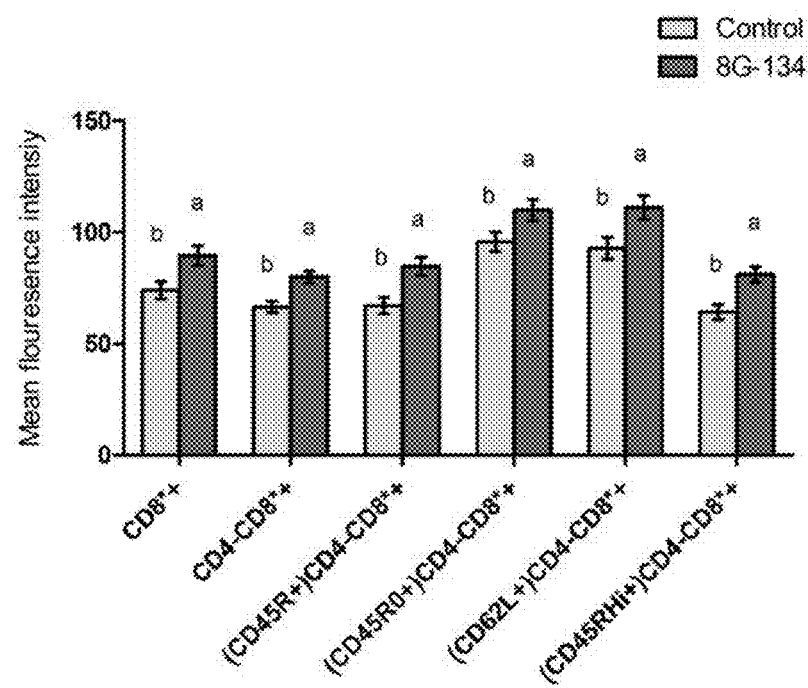
FIG. 10 is a bar graph depicting mean fluorescence intensity of T cell surface markers at approximately 60 days in milk in multiparous dairy cows fed *B. pumilus* 8G-134 at $5 \times 10^9$ CFU/cow/day or control (no DFM). Means within group with different superscript differ $P \leq 0.05$.
Figure 11:
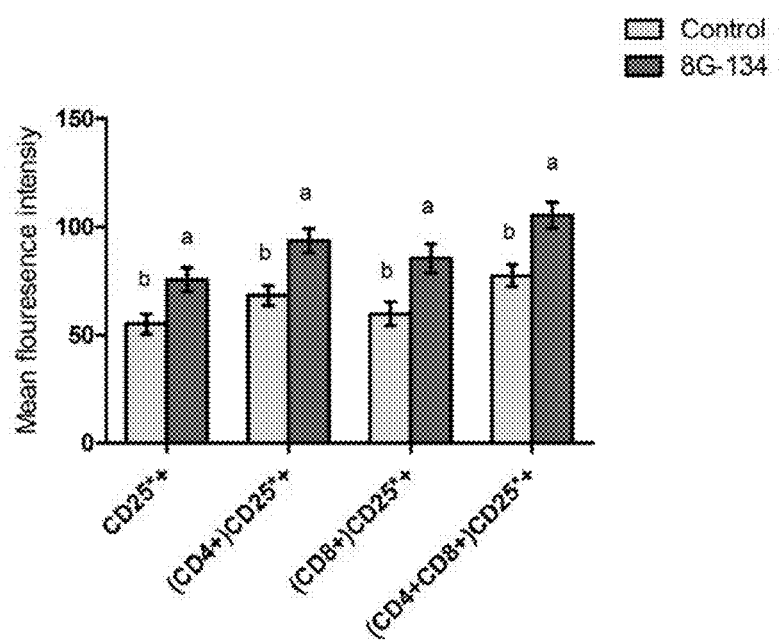
FIG. 11 is a bar graph depicting mean fluorescence intensity of T cell surface markers at approximately 60 days in milk in multiparous dairy cows fed *B. pumilus* 8G-134 at $5 \times 10^9$ CFU/cow/day or control (no DFM). Means within group with different superscript differ $P \leq 0.05$.

Milk was collected from each of 30 dairy cows at 60 days postpartum. Peripheral blood mononuclear cells in the milk were analysed by flow cytometry. Cows fed *B. pumilus* 8G-134 at $5 \times 10^9$ CFU/cow/day had increased (P<0.05) expression of T cell surface markers CD4, CD8, CD62L, CD25, and CD45RO (FIGS. 10 and 11). The enhanced expression of T cell markers may help dairy cows recover faster from immune suppression that naturally occurs during parturition, increasing resistance to mastitis and other common postpartum diseases.

Greater expression of these markers yields T cell populations that are likely more effective and efficient at combating pathogenic challenges, therefore promoting an immune response that is less costly in terms of energy expenditures to the animal. Immune suppression can lead to reproductive problems, like metritis and placental retention, and increase susceptibility to diseases like mastitis, all resulting in reduced milk yield. With administration of *B. pumilus* 8G-134, it is likely that both a more effective immune response and less postpartum disease will lead to increased energy for milk production.

Example 8

During mid-late lactation, cows must restore the body condition lost during early lactation to be able to partition energy toward fetal growth of a calf. However in helping the cow restore body condition, care must be taken to avoid overconditioning or fatness, as cows with high body condition score precalving showed higher losses in body condition postparturition that negatively affected pregnancy rates and may spend more time in a negative energy balance, resulting in metabolic disorders and reproductive problems leading to economic consequences.

It has been observed that overconditioned cows are more likely to experience ketosis, fatty liver and displaced abomasums after calving. Therefore, a healthy balance in body condition avoiding extremes of thin or overweight cows is vital for maintaining health, welfare and production performance of dairy cows. In addition, parity has an influence on a cow's ability to partition energy appropriately. It has been shown that multiparous cows with parities higher than 3 have higher body condition losses compared to primiparous cows during the first month of lactation (P<0.01), and body condition recovery by multiparous cows with parities higher than 4 was slower (P<0.01) than recovery by cows with parities lower than 3 through month 3 of lactation. This can have negative effects on longevity of the cow in production and economic outcomes.

*B. pumilus* 8G-134, when fed daily to high producing dairy cows for 12 weeks, improved milk yield by 1.62 kg/day (48.72 and 47.10 kg/day for cows with and without treatment respectively, P<0.05), but also promoted a trend toward lower milk protein % (3.04 and 3.11% for cows with and without treatment respectively, P=0.06) and a numeric decrease in milk fat % (3.58 and 3.70% for cows with and without treatment respectively, P=0.19, Table 19).

TABLE 19

Production and component least-squares means (+/−SE) by treatment with Days in Milk (DIM) category included in the statistical model for cows on study for 12 weeks

|  | Control | | *B. pumilus* 8G-134 | | |
| --- | --- | --- | --- | --- | --- |
|  | LS Mean | SE | LS Mean | SE | P-value |
| Daily Milk, kg/d[1,2] | 47.10 | 0.66 | 48.72 | 0.56 | 0.0441 |
| 3.5% Fat-Corrected Milk, kg/d[2,3,4] | 48.41 | 1.00 | 47.93 | 0.80 | 0.635 |
| Fat, %[2] | 3.70 | 0.09 | 3.58 | 0.08 | 0.190 |
| Fat, kg/d[2,3] | 1.75 | 0.05 | 1.69 | 0.04 | 0.192 |
| Protein, %[2] | 3.11 | 0.04 | 3.04 | 0.03 | 0.057 |
| Protein, kg/d[2,3] | 1.48 | 0.03 | 1.44 | 0.02 | 0.093 |
| Milk Urea Nitrogen, mg/dl[2] | 13.83 | 0.31 | 14.10 | 0.25 | 0.380 |
| SCC Log$_{10}$[5] | 1.661 | 0.08 | 1.650 | 0.07 | 0.887 |

[1]Daily milk yields after 84 days on study

[2]Model included fixed effects of pen, lactation group, DIM class (<100 DIM (62 Control cows, 75 TRT cows), 101-200 DIM (77 Control cows, 58 TRT cows), and >201 DIM (6 Control cows, 16 TRT cows)) and their two-way interactions as well as random effects of cows within pen

[3]Based on weekly mean milk yields around 3 component test days

[4]3.5% FCM, kg = ((0.4255 * Milk, lbs) + (16.425 * (% Milk fat/100)) * Milk, lbs)/2.2)

[5]Pre-Trial SCC as a covariate (P < 0.0001)

Figure 12:
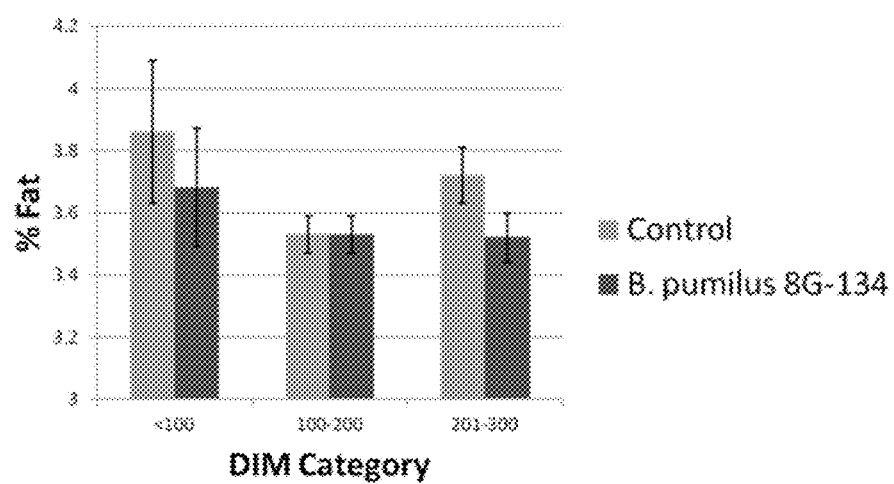
FIG. 12 is a bar graph depicting percentage milk fat in multiparous cows categorized by days in milk (DIM) over a 12 week lactation period. Days in milk (DIM) class was a covariate (<100 DIM (62 Control cows, 75 TRT cows), 101-200 DIM (77 Control cows, 58 TRT cows), and >201 DIM (6 Control cows, 16 TRT cows). Numerical decreases in fat % were observed in early and late lactation groups with DFM treatment.
Figure 13A:
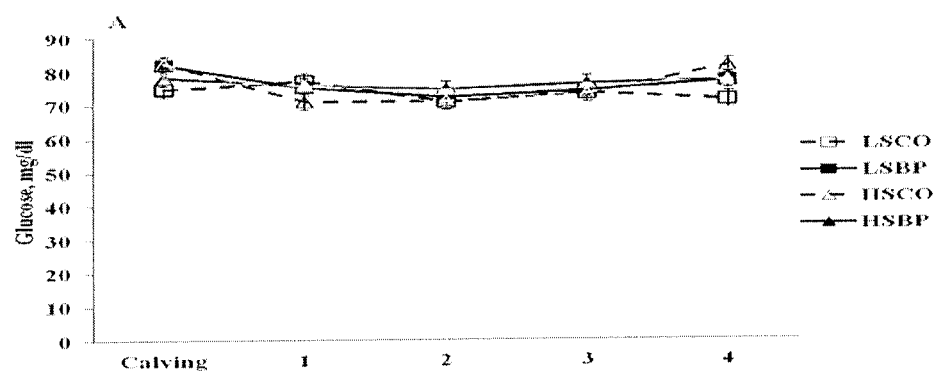
FIGS. 13A-D are line graphs depicting the association between dietary starch and *Bacillus pumilus* concentration on postpartum serum metabolites.
Figure 13B:
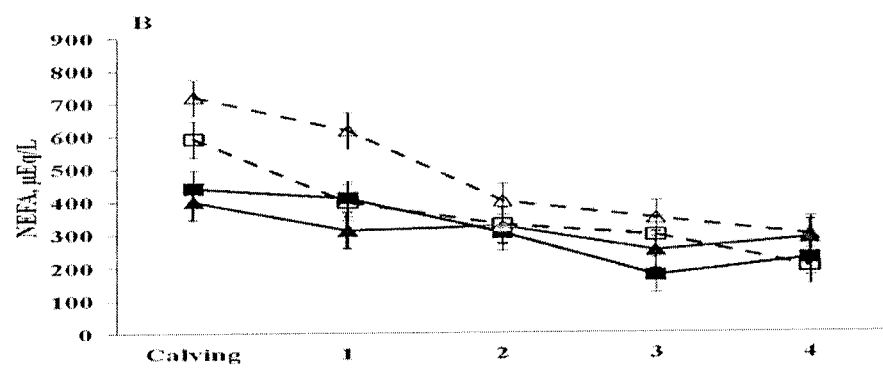
Figure 13C:
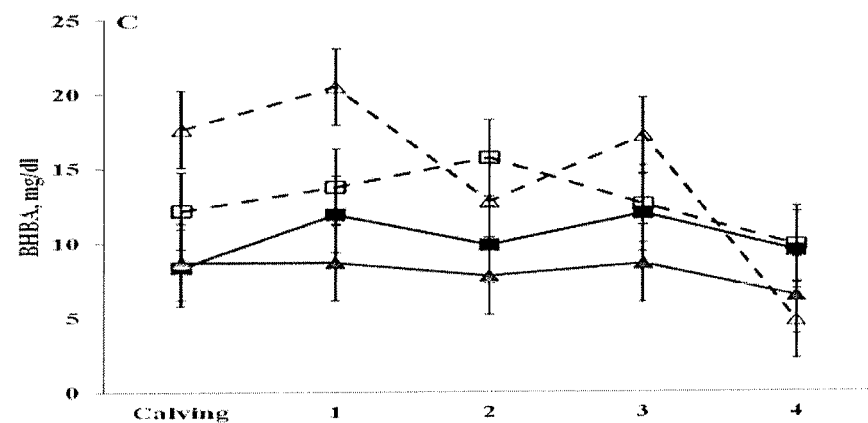
Figure 13D:
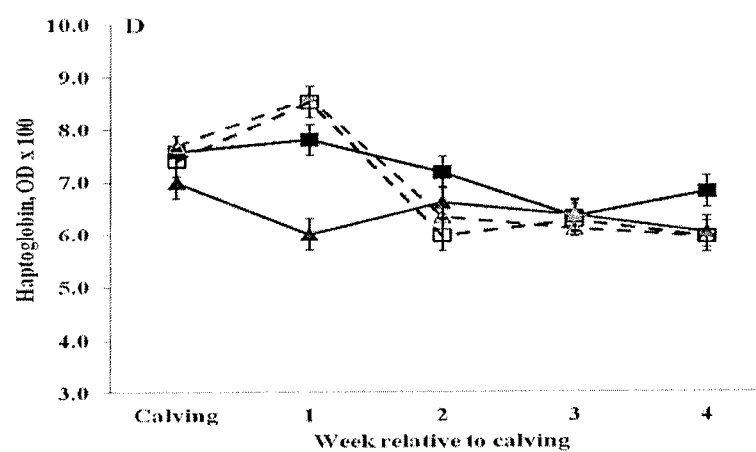

The numeric drop in milk fat was predominantly observed in early and late lactation (<100 DIM or >200 DIM, FIG. 12). Improved persistency in milk production was also demonstrated as late lactation cows (>200 DIM) receiving the *B. pumilus* 8G-134 treatment had a trend toward increased milk production (+2.01 kg/day, P=0.06) than control animals. Improving persistency of milk production during late lactation is one strategy that can be utilized to prevent overconditioning. Our results suggest that *B. pumilus* 8G-134 supplementation altered energy absorption and partitioning toward a more efficient utilization. Supplementation with *B. pumilus* 8G-134 may help to promote appropriate energy partitioning during the full lactation period, supporting improved body condition and energy balance as cows reach the dry period.

Taken together, results suggest that *B. pumilus* 8G-134 is influencing the energy balance of dairy cows through an immunomodulatory mechanism, having downstream beneficial impacts on metabolic markers (including NEFA and BHBA), metabolic diseases (SCK and RP), and milk production. It is anticipated that greater reproductive efficiency will be a result of *B. pumilus* 8G-134 administration.

Example 9

Material and Methods

The materials and methods are as described in Example 5.

Results

Postpartum NEFA concentration was unaffected by starch (P=0.29), but it was lower (P=0.05) for BP supplemented treatments (see Table 20). Cows assigned to LSBP had 52.2 µEq/L lower NEFA concentration compared with LSCO and HSBP had 161 µEq/L lower NEFA concentration compared with HSCO.

TABLE 20

Least squares means of early lactation (weeks 1-4)
serum metabolites for multiparous cows

| | Treatments[1] | | | | | P-value | | |
|---|---|---|---|---|---|---|---|---|
| | LS | | HS | | | | | |
| Variables | CO | BP | CO | BP | SEM | S[2] | BP[3] | S * BP[4] |
| NEFA,[5] µEq/L | 363.95 | 311.66 | 475.85 | 314.84 | 68.80 | 0.29 | 0.05 | 0.33 |
| BHBA,[5] mg/dl | 12.76 | 10.27 | 14.52 | 8.02 | 2.57 | 0.92 | 0.07 | 0.41 |

[1]Low starch pre- and postpartum + carrier postpartum (LSCO); Low starch pre- and postpartum + *Bacillus pumilus* postpartum (LSBP); High starch pre- and postpartum + carrier postpartum (HSCO); High starch pre- and postpartum + *Bacillus pumilus* postpartum (HSBP). Prepartum diets: LS (12% starch), and HS (19% starch). Postpartum diets: LS (20% starch), and HS (27% starch). The amount of 28 g/d of powder product was topdressing on TMR proving $5 \times 10^9$ CFU/head/day of *Bacillus pumilus* (BP).
[2]Starch effect.
[3]*Bacillus pumilus* effect.
[4]Interaction of starch and *Bacillus pumilus*.
[5]Blood collected on d 7, 14, 21 and 28 after calving.

Moreover, NEFA concentration was consistently greater for LSCO and HSCO compared with LSBP and HSBP, respectively, throughout the 28 d after calving (FIG. 13). Similarly, lower NEFA concentrations for cows supplemented with BP, reflected in a tendency (P=0.07) of lower BHBA concentrations for the same treatments. Cows assigned to LSBP tended to have 2.5 mg/dl lower BHBA concentration than LSCO, and HSBP had 6.5 mg/dl lower BHBA concentration than HSCO. Furthermore, BHBA concentration was consistently greater for LSCO and HSCO compared with LSBP and HSBP, respectively, throughout the 28 d after calving (FIG. 13).

*Bacillus pumilus* supplementation could be advantageous when fed to early lactation cows due to a reduction in NEFA and a reduction in BHBA, which demonstrates a decrease in body lipid mobilization.

It is understood that the various preferred embodiments are shown and described above to illustrate different possible features described herein and the varying ways in which these features may be combined. Apart from combining the different features of the above embodiments in varying ways, other modifications are also considered to be within the scope described herein. The invention is not intended to be limited to the preferred embodiments described above.

BIBLIOGRAPHY

Allison, M. J., M. Robinson, R. W. Dougherty, and J. A. Bucklin. 1975. Grain overload in cattle and sheep: Changes in microbial populations in the cecum and rumen. Amer. J. Vet Res. 36:181.
Dunlop, R. H. 1972. Pathogenesis of ruminant lactic acidosis. Adv. Vet Sci. Comp. Med. 16:259.
Elam, C. J. 1976. Acidosis in feedlot cattle: Practical observations. J. Anim. Sci. 43:898.
Hungate, R. E., R. W. Dougherty, M. P. Bryant, and R. M. Cello. 1952. Microbiological and physiological changes associated with acute indigestion in sheep. Cornell Vet. 42:423.
Muir, L. A., E. L. Rickes, P. F. Duquette, and G. E. Smith. 1981. Prevention of induced lactic acidosis in cattle by thiopeptin. J. Anim. Sci. 52:635.
Owens, F. N., Secrist, D. S., Hill, W. J., Gill, D. R. 1998. Acidosis in cattle: a review. J. Anim. Sci. 76:275-286.
Slyter, L. L. 1976. Influence of acidosis on rumen function. J. Anim. Sci. 43:910.
Yang, W., 2004. Effects of direct-fed microbial supplementation on ruminal acidosis, digestibility, and bacterial protein synthesis in continuous culture. Animal Feed Science and Technology, 114(4): 179-193.

What is claimed is:

1. A method for reducing negative energy balance in a dairy cow comprising:
    (a) identifying a dairy cow at risk for negative energy balance; and
    (b) administering to the dairy cow identified in step (a) an effective amount in the range of $5 \times 10^8$ CFU/animal/day to about $5 \times 10^{10}$ CFU/animal/day of live *Bacillus pumilus* strain 8G-134 (NRRL B-50174) or a live strain having all of the identifying characteristics of *Bacillus pumilus* strain 8G-134 (NRRL B-50174) to reduce negative energy balance.

2. The method of claim 1, wherein the dairy cow is a postpartum dairy cow.

3. The method of claim 1, wherein the dairy cow is a peripartum dairy cow.

4. The method of claim 1, further wherein administering to the dairy cow identified in step (a) an effective amount in the range of $5 \times 10^8$ CFU/animal/day to about $5 \times 10^{10}$ CFU/animal/day of live *Bacillus pumilus* strain 8G-134 (NRRL B-50174) or a live strain having all of the identifying characteristics of *Bacillus pumilus* strain 8G-134 (NRRL B-50174) decreases levels of nonesterified fatty acids by at least 1% or beta-hydroxybutyrate by at least 1% in the blood of the multiparous dairy cow to which is administered the effective amount of live *Bacillus pumilus* strain 8G-134 (NRRL B-50174) or a live strain having all of the identifying characteristics of *Bacillus pumilus* strain 8G-134 (NRRL B-50174) when compared to the levels of nonesterified fatty acids or beta-hydroxybutyrate in the blood of a multiparous dairy cow not administered the effective amount of live *Bacillus pumilus* strain 8G-134 (NRRL B-50174) or a live strain having all of the identifying characteristics of *Bacillus pumilus* strain 8G-134 (NRRL B-50174).

5. The method of claim 1, further wherein administering to the dairy cow identified in step (a) an effective amount in the range of $5 \times 10^8$ CFU/animal/day to about $5 \times 10^{10}$ CFU/animal/day of live *Bacillus pumilus* strain 8G-134 (NRRL B-50174) or a live strain having all of the identifying characteristics of *Bacillus pumilus* strain 8G-134 (NRRL B-50174) increases milk yield in the dairy cow by greater than 0.1% as compared to milk yield of a dairy cow not administered an effective amount of *Bacillus pumilus* strain 8G-134 (NRRL B-50174) or a strain having all of the identifying characteristics of *Bacillus pumilus* strain 8G-134 (NRRL B-50174).

* * * * *